US010302556B2

(12) United States Patent
Yost et al.

(10) Patent No.: US 10,302,556 B2
(45) Date of Patent: May 28, 2019

(54) OPTICALLY STIMULATED ELECTRON EMISSION MEASUREMENT DEVICE AND METHOD FOR CHARACTERIZING AND COMPARING LEVELS AND SPECIES OF SURFACE CONTAMINANTS

(71) Applicant: The United States of America, as represented by the Administrator of the National Aeronautics and Space Administration, Washington, DC (US)

(72) Inventors: William T. Yost, Newport News, VA (US); Daniel F. Perey, Yorktown, VA (US)

(73) Assignee: THE UNITED STATES OF AMERICA AS REPRESENTED BY THE ADMINISTRATOR OF NASA, Washington, DC (US)

(*) Notice: Subject to any disclaimer, the term of this patent is extended or adjusted under 35 U.S.C. 154(b) by 170 days.

(21) Appl. No.: 15/210,444

(22) Filed: Jul. 14, 2016

(65) Prior Publication Data
US 2017/0067819 A1 Mar. 9, 2017

Related U.S. Application Data

(60) Provisional application No. 62/214,232, filed on Sep. 4, 2015.

(51) Int. Cl.
G01N 21/27 (2006.01)
G01N 21/33 (2006.01)
G01N 23/2273 (2018.01)

(52) U.S. Cl.
CPC ......... G01N 21/272 (2013.01); G01N 21/33 (2013.01); G01N 23/2273 (2013.01);
(Continued)

(58) Field of Classification Search
None
See application file for complete search history.

(56) References Cited

U.S. PATENT DOCUMENTS 4,590,376 A 5/1986 Smith
4,945,239 A 7/1990 Wist et al.
(Continued)

FOREIGN PATENT DOCUMENTS

EP 0172477 A2 2/1986
JP 2011007700 A2 1/2011

OTHER PUBLICATIONS

Mattes, R.A., Contamination Monitoring of RSRM Bonding Surfaces Using OSEE, 1989, Proceedings—Institute of Environmental Sciences, pp. 383-391.*
(Continued)

Primary Examiner — Xiaoyun R Xu
(74) Attorney, Agent, or Firm — Andrea Z. Warmbier; Robin W. Edwards; Mark P. Dvorscak

(57) ABSTRACT

Systems, methods, instruments and devices of the various embodiments enable improved characterization and comparison of the level and species of surface contaminants from photo-induced emission analysis. The various embodiments may provide flexibility for calculating and analyzing the time-dependence of emission efficiencies. Irregular and heterogeneous surfaces, including regionally multiply-connected surface compositions, may be analyzed according to the various embodiments, and the various embodiments include techniques that support specific contaminant identification. Various embodiment focusing techniques may enhance assessment of spatially differential regional analysis of the substrate for more critical applications. The various embodiments may also include differential comparison with reference surfaces, either through differential com-
(Continued)

parison while scanning, or by comparison to digitally stored responses to known contaminants.

12 Claims, 18 Drawing Sheets

(52) U.S. Cl.
CPC . *G01N 2201/062* (2013.01); *G01N 2201/068* (2013.01); *G01N 2201/06113* (2013.01)

(56) References Cited

U.S. PATENT DOCUMENTS

| | | | |
|---|---|---|---|
| 5,028,778 A | 7/1991 | Ninomiya et al. | |
| 5,097,126 A | 3/1992 | Krivanek | |
| 5,185,524 A | 2/1993 | Page | |
| 5,260,584 A | 11/1993 | Popson et al. | |
| 5,289,004 A | 2/1994 | Okada et al. | |
| 5,393,980 A | 2/1995 | Yost et al. | |
| 6,480,285 B1 | 11/2002 | Hill | |
| 6,856,403 B1 | 2/2005 | Welch et al. | |
| 2012/0080616 A1* | 4/2012 | Schoenborn | A61B 5/0059 250/459.1 |
| 2012/0235036 A1 | 9/2012 | Hatakeyama et al. | |

OTHER PUBLICATIONS

Maurer, R. J., "Handbook of Physics," Chapter 5, E.U. Condon and H. Odishaw, McGraw Hill, 1967, New York, pp. 8-67 to 8-75.
Welch, C. S. et al., "OSEE Inspection of Solid Rocket Motor Steel," NASA Conference Publication 3139, Third Conference on NDE for Aerospace Requirements, pp. 200-237, Jun. 1991.
PCT International Search Report PCT/US2016/049672 pp. 1-7, dated Nov. 14, 2016.
PCT International Preliminary Report on Patentability, PCT/US2016/049672, dated Mar. 6, 2018, 5 pages.

\* cited by examiner

OPTICALLY STIMULATED ELECTRON EMISSION MEASUREMENT DEVICE AND METHOD FOR CHARACTERIZING AND COMPARING LEVELS AND SPECIES OF SURFACE CONTAMINANTS

CROSS-REFERENCE TO RELATED PATENT APPLICATION

This patent application claims the benefit of and priority to U.S. Provisional Patent Application Ser. No. 62/214,232, filed on Sep. 4, 2015, the entire contents of which are hereby incorporated by reference in their entirety.

STATEMENT REGARDING FEDERALLY SPONSORED RESEARCH OR DEVELOPMENT

The invention described herein was made by employees of the United States Government and may be manufactured and used by or for the Government for governmental purposes without the payment of any royalties thereon or therefore.

BACKGROUND OF THE INVENTION

Monitoring the quality and conditions of a surface can be advantageous for array of manufacturing processes. For example, the indication, identification, and quantification of contaminants such as grease or dirt are vital in painting or coating processes, forming laminates, applying adhesives, etc. The identification of contaminant species and their levels are important because species and levels are factors as possible progenitors of bond failure modes. While the exact mechanisms can vary, it is widely held that surface contaminants interfere with formation of surface to adhesive bonding, either through the mechanisms of interference with density of bonds between the surface and the adhesive, or by diffusion-related processes of contaminant into the adhesive, which may lead to a weakening of cohesion within the adhesive itself. The effects of these processes are verified by several tests, including by peel tests, where the adhesive layer is essentially peeled away from the substrate. For example, peel tests of surface contamination levels of grease remaining on a steel substrate have demonstrated that surface contamination reduces bond strength. In critical bonds, therefore, a determination of contamination level of surface, prior to application of adhesives, may be essential.

BRIEF SUMMARY OF THE INVENTION

The systems, methods, and devices of the various embodiments enable improved characterization and comparison of level and species of surface contaminants from photo-induced emission analysis. The various embodiments may provide flexibility for calculating and analyzing the time-dependence of emission efficiencies. Irregular and heterogeneous surfaces, including regionally multiply-connected surface compositions, may be analyzed according to the various embodiments, and the various embodiments include techniques that support specific contaminant identification. Various embodiments of focusing techniques may enhance assessment of spatially differential regional analysis of the substrate for more critical applications. The various embodiments may also include differential comparison with reference surfaces, either through differential comparison while scanning, or by comparison to digitally stored responses to known contaminants. The various embodiments may work with multiple contaminants on substrates, such as structural components fabricated from carbon fiber composite materials, polymers reinforced with carbon nanotubes, conductive-coated (e.g. beryllium coated mirrors), specialized coatings (metallic and non-metallic) on various substrates, and metallic surfaces.

These and other features, advantages, and objects of the present invention will be further understood and appreciated by those skilled in the art by reference to the following specification, claims, and appended drawings.

BRIEF DESCRIPTION OF THE SEVERAL VIEWS OF THE DRAWINGS

The accompanying drawings, which are incorporated herein and constitute part of this specification, illustrate exemplary embodiments of the invention, and together with the general description given above and the detailed description given below, serve to explain the features of the invention.

DETAILED DESCRIPTION OF THE INVENTION

Figure 1A:
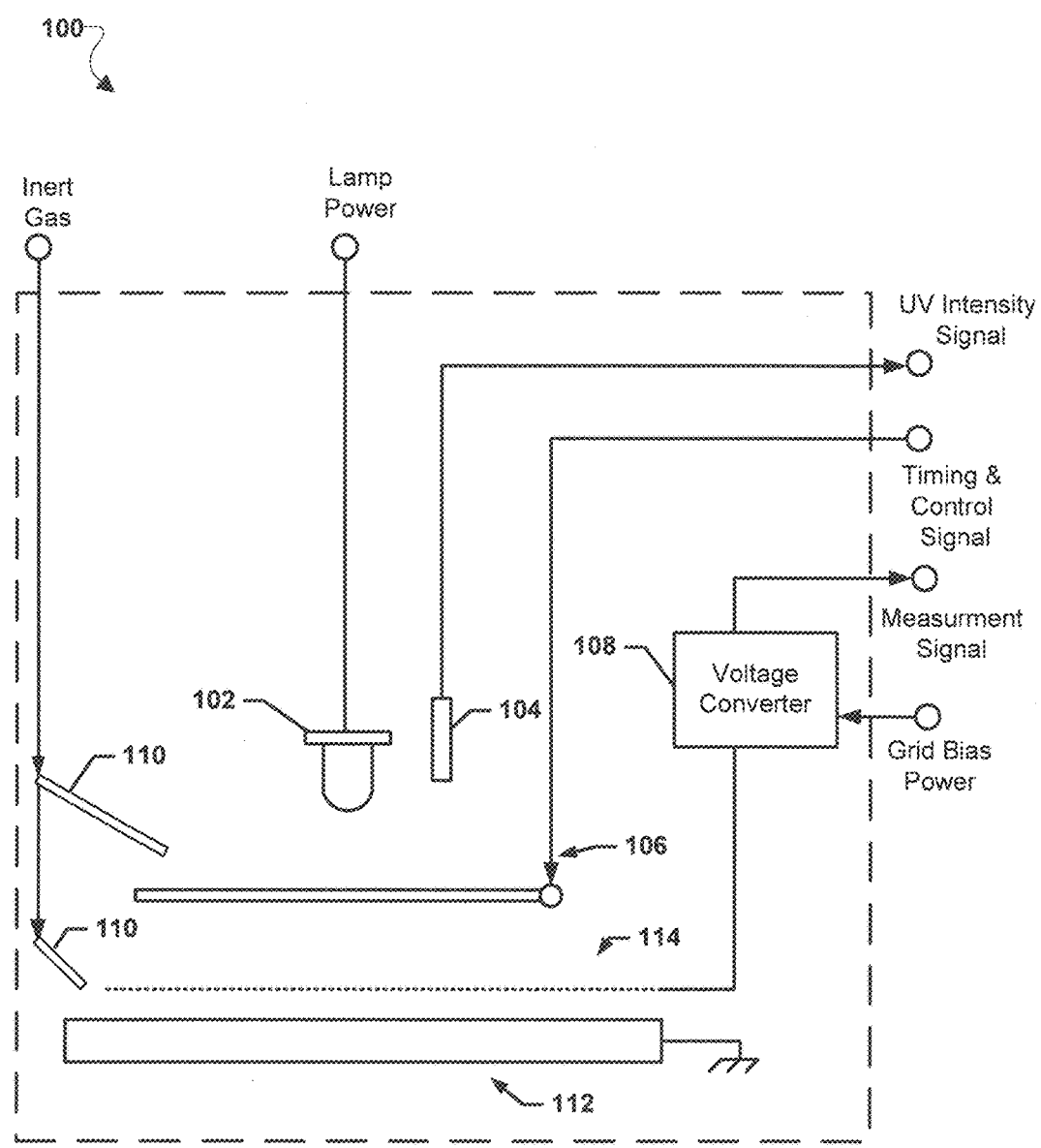
FIGS. 1A and 1B illustrate elements of an optically stimulated electron emission (OSEE) measurement device or instrument according to an embodiment.

For purposes of description herein, it is to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The word "exemplary" is used herein to mean "serving as an example, instance, or illustration." Any implementation described herein as "exemplary" is not necessarily to be construed as preferred or advantageous over other implementations.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

The instrument outlined in U.S. Pat. No. 5,393,980 (the entire contents of which are incorporated by reference herein) and the variety of light (wavelength) sources and filtration capabilities, as outlined in U.S. Pat. No. 6,856,403 (the entire contents of which are incorporated by reference herein) may provide quality monitoring techniques employing optically stimulated electron emission (OSEE). The instrument is based on the photoelectric emission from the substrate and the analysis is based solely on photoelectron emission current, which is compared to similar currents emitted from clean surfaces. Hence, given two surfaces of the same material, where one is known to be clean, a comparison of the emitted photoelectric currents from the two surfaces permits an accurate estimate of the levels of contamination on the unknown surface.

The instruments and methods outlined in U.S. Pat. Nos. 5,393,980 and 6,856,403 were designed to operate with metallic surfaces. The instrument design depends upon regular flat (or large radius of curvature) surfaces, and measurements, and which show definite effects from humidity. The instruments and methods outlined in U.S. Pat. Nos. 5,393,980 and 6,856,403 do not make use of time dependence of photocurrents for analytical imposes leading to identification of the contaminant species, and do not include means for swept or modulated electromagnetic illumination wavelength capability to aid in a more accurate identification of contaminant species. Nor do the instruments and methods outlined in U.S. Pat. Nos. 5,393,980 and 6,856,403 allow for differential comparisons of surfaces in real time, nor adjustments for different emitting surfaces within the same structure, as so often occurs at joining composite-to-composite and/or composite-to-metal junctions to be bonded with adhesives. The instruments and methods outlined in U.S. Pat. Nos. 5,393,980 and 6,856,403 do not include effects from environmental factors, including temperature, humidity, dust levels, etc.

The instruments and methods outlined in U.S. Pat. Nos. 5,393,980 and 6,856,403 are based on the photoelectric effect to provide a photo-current which responds to surface contamination. The common sequence is that a contaminant absorbs or otherwise scatters the ultraviolet light illuminating the surface. The fraction of illumination that reaches the substrate interacts with the substrate-located electrons, causing an emission. This emission is attracted to a collector surface where the current is measured.

U.S. Pat. Nos. 5,393,980 and 6,856,403 teach that the contaminants absorb the photonic radiation. However, because of the technology covered by U.S. Pat. Nos. 5,393,980 and 6,856,403, the methods described in those patents can lead to erroneous results, especially when the illuminating source containing multiple wavelengths, generates complex molecular structures that interact with contaminant species in a way that alters the local surface electronic states within the contaminant's complex molecular structure, and also possibly form states, including possible complex metastable states with molecules attached to the substrate surface. These states affect localized electronic structures at the substrate's surface, and can result in enhanced or diminished photoelectron emission, and must be taken into account to analyze effects of surface contaminants that affect photoemission. The argument is either made, or implied, that these same contaminants may affect adhesive-based bonding strength. These actions can affect the localized work function and hence photo-based emission efficiencies in ways that can give currents that lead to erroneous contaminant level readings.

The systems, methods, and devices of the various embodiments enable improved characterization and comparison of level and species of surface contaminants from photo-induced emission analysis. The various embodiments may provide flexibility for calculating and analyzing the time-dependence of emission efficiencies. Irregular and heterogeneous surfaces, including regionally multiply-connected surface compositions, may be analyzed according to the various embodiments, and the various embodiments include techniques that support specific contaminant identification. The various embodiments ability to provide for this degree of highly informative inspections may permit the operator of an embodiment system to determine those procedures that assure a more successful bonding of significant coatings by localizing the contaminant, and hence the preferred solvent/treatment to clean each local region of the surface for optimum bonding results. Various embodiment focusing techniques may enhance assessment of spatially differential regional analysis of the substrate for more critical applications. The various embodiments may also include differential comparison with reference surfaces, either through differential comparison while scanning, or by comparison to digitally stored responses to known contaminants. New procedures enabled by the various embodiments may allow for measurements that minimize exposures of surfaces to ultraviolet exposures to reduce effects of photo-induced chemical reactions that may affect bond strength. The various embodiments may work with structural components fabricated from carbon fiber composite materials, polymers reinforced with carbon nanotubes, conductive-coated (e.g. beryllium coated mirrors), specialized coatings (metallic and non-metallic) on various substrates, and metallic surfaces, and including substrate surfaces with multiple contaminants. Additionally, the various embodiments may be applied in scanning systems for large acreage applications, including raster and array scanning techniques.

The various embodiments provide for quicker data-taking and data analysis in real time, and various embodiments may be easily adapted into scanning applications. The analysis algorithms based on the interactions induced by multiple wavelengths enable identification of contaminant species and concentration through differential scan techniques, time-current analysis, and its relationship to the underlying surface chemistry. Various embodiments may provide a differential scanning capability. Various embodiments may provide an ability to accurately interrogate irregular shaped surfaces, such as fillets, bolt threads, etc. Various embodiments may aid in identification of contamination. Various embodiments may incorporate physical models to aid in more dependable results and predictions. Various embodiments may improve identification of surface chemistry effects that lead to identification of chemical processes. Various embodiments may minimize the exposure to UV radiation.

An embodiment device or instrument may measure low levels of surface contamination on surfaces with various construction, contours, and shapes. The information provided by the embodiment device may improve analysis of surface preparation needed for more reliable adhesive bonding, a technique that is becoming more important in lighter weight (and hence more fuel efficient) aircraft and spacecraft. A major factor in adhesive bond durability is contamination left behind by surface preparation techniques. It has been shown that contamination species and concentration levels are major contributors to adhesive bond failures (a "contaminant'" in this context is any substance that interferes with the bonding process between an adhesive and a surface). Present assembly techniques include blends of materials chosen for specific stress levels and local environments sustained by the assembly. This necessitates possible adhesive attachments of structures made from dissimilar materials. Even within similar materials, blends within composites can result in a range of dissimilar surfaces to be bonded, each with different responses to contaminant species and levels.

Various embodiments may enable exposure control to: eliminate overexposure-related surface damage; provide provisions to simultaneously record surfaces of differing materials and different shapes; and identify contaminating species. Additionally, various embodiments may enable the excitation of surface chemistry and the identification of contaminant species from analysis of derivatives of collector currents during a (brief) exposure to the ultraviolet radiation. In various embodiments, the combination of the exposure and radiation mixture may excite a variety of time-dependent chemical reactions, which may also contribute to the collector current, along with the optically stimulated electron emission (OSEE) from the substrate.

The various embodiments may provide the ability to examine the time dependence of the current to make possible the identification of the contaminant species on substrates. This may apply to materials other than the metal or insulating substrate, such as surfaces of composite materials, and materials composed of nano materials such as carbon nanotubes. With an increase of the number and variety of attachment sites on such substrates, more and different bond failure mechanisms may be possible.

In the various embodiments, the Langmuir model of chemisorption and the photo charge emission characteristics of the variety of substrates may be used to aid in the species identification. In the various embodiments, once identified, the effects of the contaminant species and its concentration on the service life of an adhesive joint can be determined. Each surface contains a number of sites for molecular contaminant attachment, which are activated by photo-excitation from the mercury discharge illumination source in the various embodiments. These active sites alter attachment probabilities of the molecular complexes that make up the contaminants. This alteration, especially those activated by photo-excitation, affect local work functions of the substrate, and/or change the polarization state of dipoles on or within the substrate. In either case, a change in the photo-induced current collected by the OSEE collection electrode system may occur in response to the illuminating radiation. The various embodiment instruments may be configured to determine the contaminant species based on the received photocurrent as a function of time.

Exposures to UV radiation, which may be a necessary ingredient for the various embodiment applications of photoemission from the expanded sets of substrates, affects surface condition, especially surfaces that contain carbon-based and polymeric materials. Therefore, light intensity controls of the various embodiment instruments allow for sufficient signal to noise ratios, and provide limitations through exposure controls. Light intensity controls of the various embodiments may take several forms including, intensity controls and mechanisms to limit exposure time.

The emitted electron collection by a spatially uniform and constant electric field for collecting electrons may be a necessary design feature for the various embodiments to assure measurements that relate to true physical variables for accurate interpretations. For example, the electron emission current (in pico-Amps (pA)), may be directly related to charge emission current density, and may depend upon numerical photon intensity. In one embodiment device that uses a mercury-discharge source, the embodiment instrument may regulate intensity to a known and adjustable level by monitoring the intensity of a single line, such as the 2536 Angstrom (Å) line, from the mercury-discharge tube.

Figure 1B:
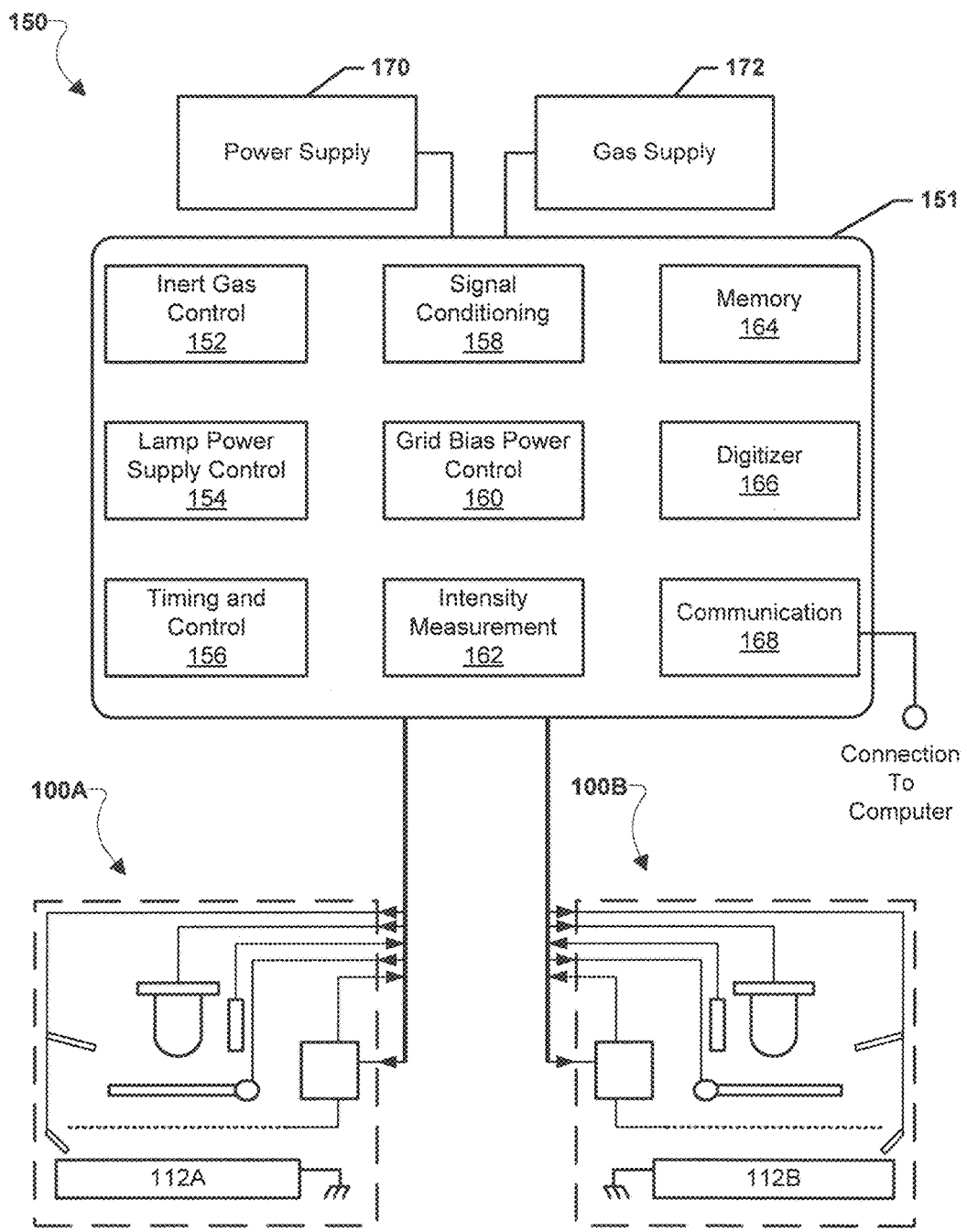

FIGS. 1A and 1B illustrate elements of an instrument according to an embodiment of the present invention. Configurations and operating concepts of various features of the embodiment pods and instrument 150 described with reference to FIGS. 1A and 1B may be similar to some features of the instruments described in U.S. Pat. Nos. 5,393,980 and 6,856,403. An embodiment of an optically stimulated electron emission (OSEE) measurement pod 100 of an embodiment of an instrument 150 (discussed below with reference to FIG. 1B) is illustrated in FIG. 1A. The pod 100 may include one or more lamp(s) 102, one or more purge gas nozzle(s) 110, a shutter 106, a voltage converter 108, a grid 114, and a sample holder supporting a sample 112.

The lamp 102 may be any type lamp capable of producing light from the electromagnetic spectrum. The lamp 102 may be a continuous spectrum lamp with content in the visible region, such as an arc or tungsten lamp. The lamp 102 may be a source made from one or several laser emitters or light emitting diode (LED) emitters and/or the lamp 102 may also be a discharge tube or flash tube capable of producing multiple wavelengths. While illustrated as a lamp 102 in each respective pod 100, the lamp 102 may be a single source outside the pod 100 with light pipes conducting the radiation flux to one or more pods. The lamp 102 may include structures configured to focus the rays from the light (e.g., one or more lenses, apertures, reflectors, etc.). A charge collector (with a positive bias voltage) may also be attached to the lamp 102. The lamp 102 may be connected to a power supply 170 (FIG. 1B) and a lamp power supply control module 154 (FIG. 1B). The intensity of the lamp 102 may be monitored by the ultraviolet (UV) intensity monitor 104 which may output UV intensity signals to the intensity measurement module 162 (FIG. 1B). The intensity measurement results from the intensity measurement module 162 (FIG. 1B) may be used by the lamp power supply control module 154 (FIG. 1B) to actively control the lamp 102 intensity by regulating the lamp power provided to the lamp 102, such as through a feedback loop. The lamp 150 may be single or multiple coherent light sources, examples being diode-emitting sources, (i.e. laser emitting sources) with emission frequencies chosen to optimize a response to specific contaminants of interest.

The purge gas nozzle 110 may provide an inert gas, such as argon, to the pod 100, and the flow of the inert gas may be controlled by the inert gas module 152 (FIG. 1B) regulating the flow of gas from a gas supply 172 (FIG. 1B), for example via opening/closing one or more controllable valves of a gas manifold connected to the pod 100.

The shutter 106 may open and close as controlled by a timing and control module 156 (FIG. 1B) to start/stop light from the lamp 102 hitting the sample 112.

The voltage converter 108 may be connected to the grid 114 which may be biased by the grid bias power provided to the grid 114 (FIG. 1A) from a power supply 170 (FIG. 1B) as controlled by the grid bias power control 160 (FIG. 1B).

The grid 114 and/or a separate collection electrode may collect emitted electrons and ions from the sample 112 when it is illuminated by the lamp 102 and opening of the shutter 106, and the emitted electrons and ions collected as a function of time may be converted to a current, which may be output as a measurement signal to the signal conditioning module 158 (FIG. 1B).

As illustrated in FIG. 1B, the embodiment instrument 150 may include (or be connected to) a power supply 170 and gas supply 172. The instrument 150 may include a processor 151, such as a microcontroller, including a inert gas control module 152, lamp power supply control module 154, timing and control module 156, signal conditioning module 158, grid bias power control module 160, intensity measurement module 162, memory 164, digitizer 166, and communication module 168. The instrument may include one or more pods, such as two pods 100A and 100B, more than two pods, etc., connected to the processor 151. The digitizer 166 may convert analog inputs to digital outputs. The signal condition module 158 may apply signal processing techniques and analysis algorithms to the measurement signals received from the pods 100A and 100B. The memory 164 may store past measurements, reference measurements used for difference measurements, and/or results from signal processing and analysis performed by the signal conditioning module 158. Via the communication module 168, the instrument 150 may receive and/or output data from/to one or more connected computers and/or networked devices.

The instrument 150 may additionally include an accompanying gas sensor(s) that may be incorporated so that as gases are formed from the UV exposures, the gases may be monitored. This may be especially valuable for determining the UV exposure intensity levels that alters a polymer's surface structure, as a warning that structural changes that may affect the structural strength within the substrate may be occurring.

In operation the embodiment instrument 150 may be cycled through a sequence of events to generate a measurement. First, using argon or a similar inert gas, a purge of the chamber and surrounding region to include the sample region of the sample 112 may be started. Depending on application, the purge may be continuous to prevent interferences from gas and water vapor contamination of the surface from exposure to atmospheric air. Next, the lamp 102 may be activated, and is verified to be consistently emitting in the intensity range chosen by the operator, for example by the intensity measurement module 162. This condition may be maintained throughout the measurement operation. Next, at a predetermined point in time the shutter 106 may be opened and the light floods a preselected and known area of the sample 112. Emitted electrons and ions may be collected as a function of time, converted into a current from which to measure current density (current/area) and converted, as needed, to charge number per unit area over time, or numerical current density. The initial numerical current value may be related to a numerical photon intensity (photons/area per unit time) striking the surface of the sample 112 under examination immediately following the opening of the shutter. The time record following the opening may be digitized by the digitizer 166 and recorded and stored in memory 164 for analysis for a time interval that includes sufficient time for the photo-related chemical reactions to occur, The appropriate quantities may be calculated as needed, for chemical identification and concentration calculations. After a predetermined time the shutter 106 closes, and the measurement may be completed. The length of time that the shutter 106 is opened may depend upon a number of factors. For example, if one only wants to use the substrate's photoelectrons for analysis, the shutter 106 may be closed very shortly after full opening. This action avoids effects of the onset of metastable state formation that occurs in a luminous field. For the test instrument constructed for this analysis, the time interval for exposure may be approximately 80 to 100 milliseconds. As another example, if the shutter 106 stays open for a period longer than approximately 80 to 100 milliseconds, the photoactivated chemistry begins to occur. This period longer than approximately 80 to 100 milliseconds may also shows the effects of the chemistry on photoemission, by altering the localized work functions, and hence change the efficiency of the photoelectric emission.

Figure 1C:
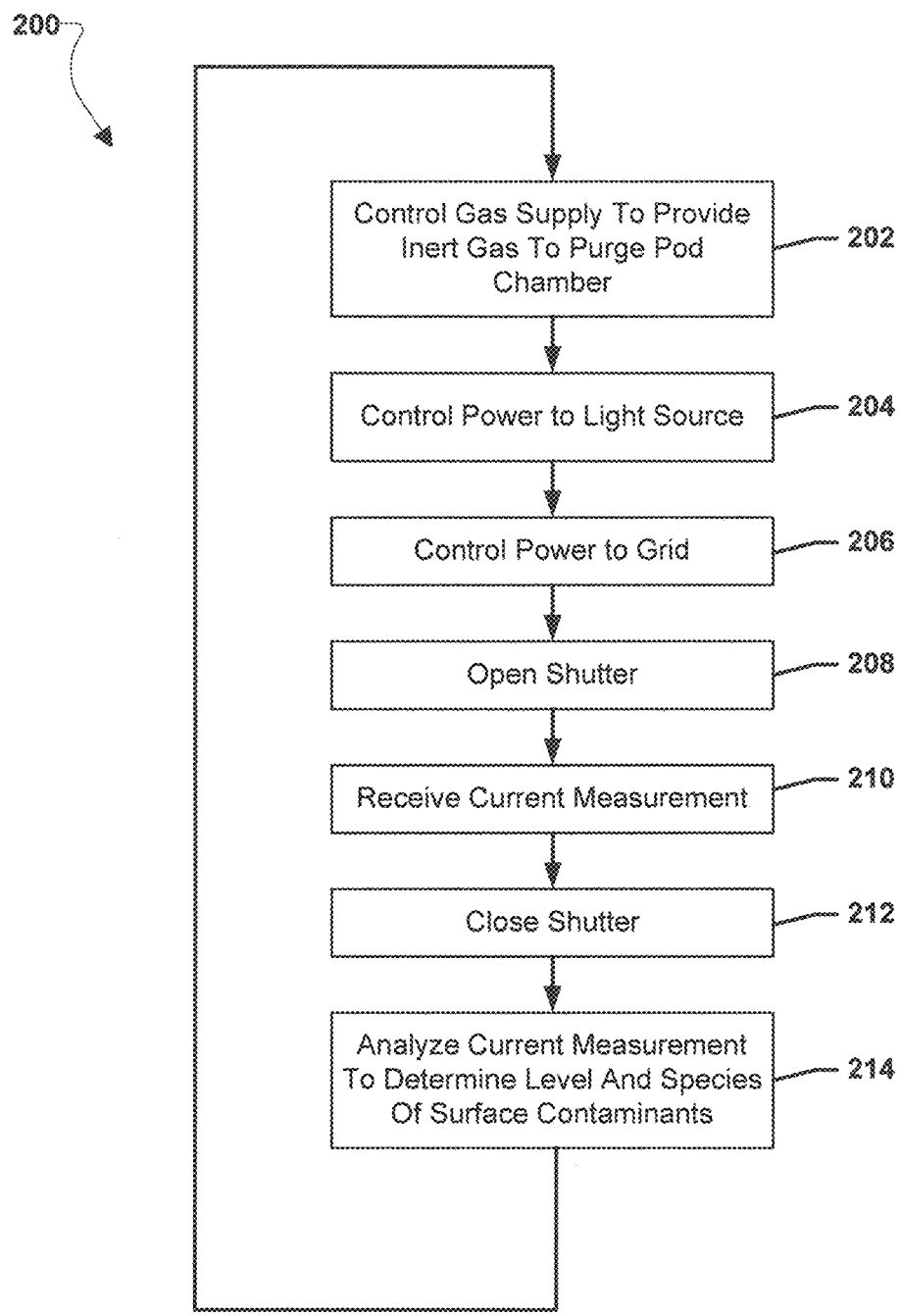
FIG. 1C is a process flow diagram illustrating an embodiment method for performing OSEE measurements.

FIG. 1C illustrates an embodiment method 200 for performing OSEE measurements. In an embodiment, the operations of method 200 may be performed by a processor of an embodiment OSEE measurement instrument, such as processor 151 of instrument 150.

In block 202 the processor may control a gas supply, such as gas supply 172, to provide an inert gas, such as argon, to purge a chamber of the pod, such as via gas nozzle 110 to purge the chamber of pod 100. In block 204 the processor may control the amount of power provided to a light source. For example, the processor 151 may control the voltage and/or current provided to the lamp 102 from the power supply 170. In an embodiment, the pod 100 may include a luminous intensity monitor, such as UV intensity monitor 104, and controlling an amount of power from the power supply to the light source to cause the light source to generate a known light intensity may include controlling the amount of power based at least in part on a signal from the UV intensity monitor to maintain an intensity of the light at a selected level. In block 206 the processor may control the power provided to the grid. For example, the processor 151 may control the voltage and/or current from the power supply 170 to the grid 114 to bias the grid 114.

In block 208 the processor may open the shutter, such as shutter 106. For example, the processor 151 may send a control signal to the shutter 106 causing the shutter to open. In block 210 the processor may receive the current measurement from the pod. In block 212 the processor may close the shutter, such as shutter 212. For example, the processor 151 may send a control signal to the shutter 106 causing the shutter to close. The length of time the shutter 106 may be opened and closed may be selected based on the intended phenomena to be measured. In block 214 the processor may analyze the received current density measurement to determine a level and a species of surface contaminants on a selected area of the sample over which the pod may be placed. In some embodiments, analyzing the current measurement may include comparing the received current measurement to data from a reference substrate stored in memory. In some embodiment, analyzing the current density measurement may include comparing the received current measurements from two different pods together to identify the differences between the measurements. For example, one pod may be placed over a reference substrate, while another pod is placed over the sample of interest. The difference between the current densities of the two pods may identify the level and species of contaminants on the sample of interest. The method 200 may be continually repeated over the same sample and/or as the one or more pods of the instrument 150 are moved to different locations.

In the various embodiments, the pods may be spatially rearranged to accommodate various geometries for inspections of different shaped parts. The pods may be arranged to accommodate the geometry of the part to be inspected. For example, pods 100A and 100B may be arranged differently on different parts to be inspected. Additional pods can be assigned to reference substrates with known contaminants and contaminant levels for differential readings. For example, pod 100A may be arranged over a substrate to be measured and pod 100B may be arranged over a reference substrate with known contaminants and contaminant levels, enabling differential readings (i.e., a difference level between pod 100A measurements and pod 100B be determined). In another embodiment, measurements for a reference substrate with the known contaminant/contaminant level may be digitally stored in memory 164 for differential comparisons.

As an example of differential readings using multiple pods, pod 100A may be set in one plane of a mating surface, and pod 100B may be set in a near-by plane, located in a different assembly, where the two assemblies are to be adhesively bonded together. Both surfaces may be scanned simultaneously. As another example, a reference surface can be simultaneously scanned by pod 100B with a surface under examination scanned by pod 100A. Differences between the two scanned surfaces can be calculated and displayed to verify contaminant level between both surfaces. Another approach may be to store a scan from a reference surface. A surface scan may be compared with the stored surface. Moreover, any surface scan may be compared with a later scan to verify effectiveness of surface preparation procedures.

No planer electrode pods may also be used in the various embodiments to obtain improved data collection around bolts and threaded joints, in welded structures, such as fillets, and in beam-forming procedures, such as occurs in electron-beam formed and 3-D printed structures. In an embodiment, these non-planar electrode pods may be coaxial in structure with the light source axially aligned with the collector electrode. In other embodiments, the electron collector may have other shapes and arrangements to facilitate the geometry of the surface being inspected.

The instrument 150 may also incorporate lock-in dynamics that permit an intensity modulation to test for contaminant interactions that aid in identification of interacting species. Such applications may use lock in amplifier techniques to follow and interpret the modulations to minimize surface UV exposures. Additionally, the instrument 150 may utilize interaction dynamics that photo-induced stresses in contaminants cause that may lead to acoustic signatures that can be picked up with simple low-frequency circuitry and sensors designed for audio frequencies.

In another embodiment a small pod in the shape of a circular foot-print may be provided, where the UV radiation is carried through an optical fiber capable of transmitting the 1849, the 2537, and other useful spectral lines in the mercury discharge source. In another embodiment, the arrangement may be similar, but with input from single or multiple laser or LED sources of appropriate wavelengths to excite the specimen's work function and photo-activation affecting chemistry in the local region. This radiation may illuminate a small surface, with an electrode arrangement to collect the consequent emission of photo-based charges. Such an arrangement may be capable of scanning regions of broken bonds to ascertain the chemistry around the broken areas.

Figure 2:
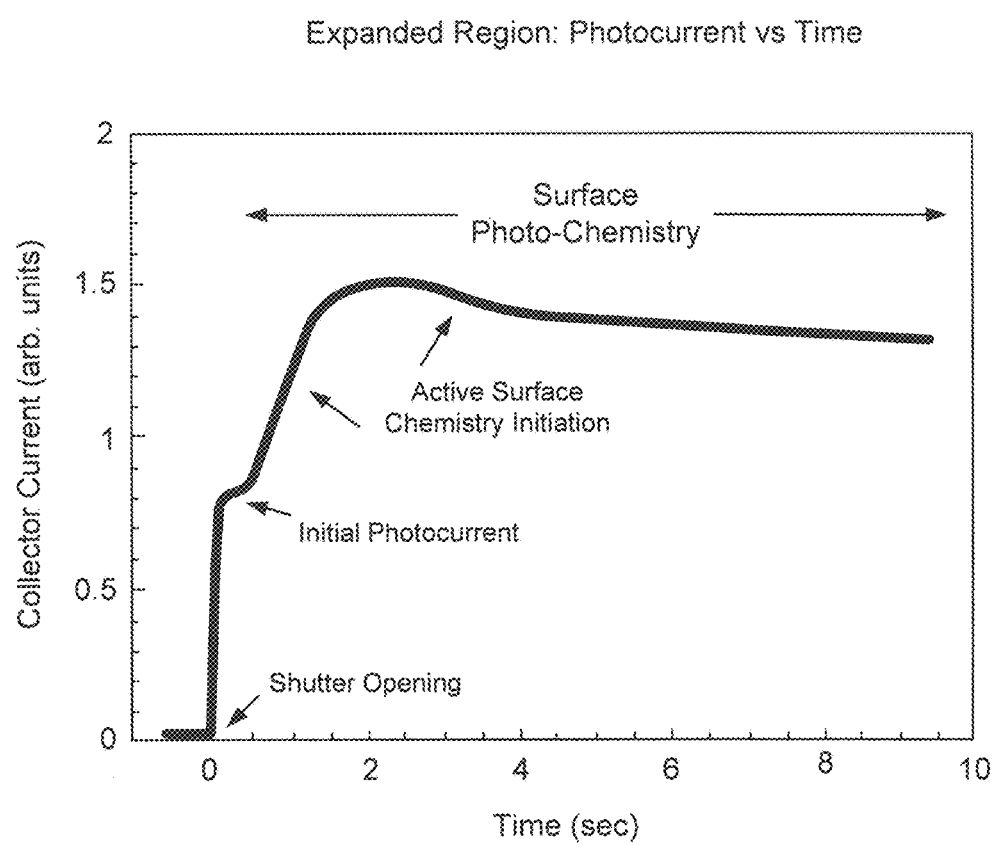
FIG. 2 illustrates an example time record of a pod according to the various embodiments.

An example time record of a pod according to the various embodiments is illustrated in FIG. 2. FIG. 2 illustrates a typical time record of collector current from a contaminated surface. Significant regions of interest include shutter opening, initial photocurrent, and active surface chemistry initiation. This time record illustrates a slice from a 10 second exposure record from a single pod of an embodiment OSEE instrument. Immediately after the shutter opens, the photocurrent jumps to a level as predicted by the photoelectric analysis, and based on the work function of the substrate, intensity and spectral profile of the illuminating source, and the contaminant's spectral absorption coefficient and thickness. The contaminant also affects the local work function value. After approximately 500 msec, a gradual rise in the photocurrent occurs over a period of several seconds, depending on the contaminant species and concentrations. A plateau lasting several more seconds is reached, after which a state of photocurrent decline begins and lasts through the remainder of the plot. The data obtained immediately after the shutter is opened may be usable. While in general, before the ultraviolet-activated chemistry-effects are initiated by a relatively lengthy exposure, possible deleterious surface effects may be avoided, especially when used to inspect surface contamination in some polymeric-based materials. Because photoelectrons are initiated within nanoseconds of photonic exposure, one can get a reading consistent with the electronics circuits within the embodiment measuring devices.

Figure 3:
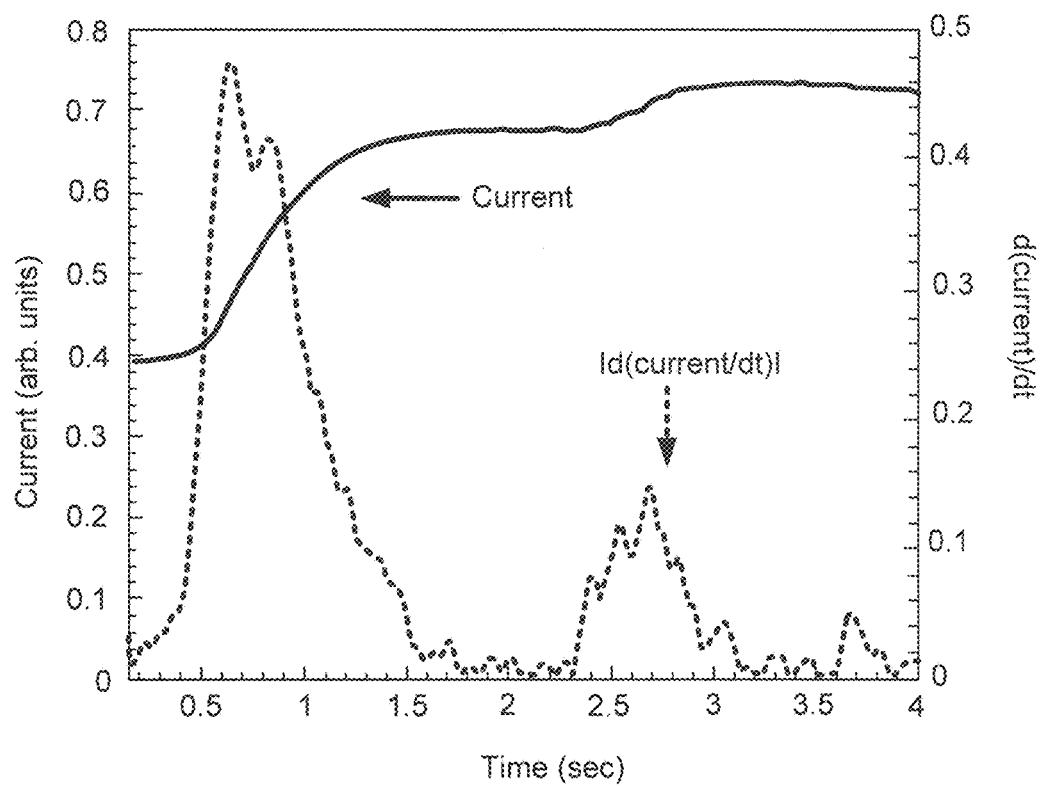
FIG. 3 is a graph illustrating current vs, time for a contaminated substrate.

The basis of the surface contaminant state analysis is set in the parameters measured during this time. To better examine the effect, a derivative of the waveform may be shown. FIG. 3 shows current vs. time for a contaminated substrate. The derivative highlights the changes in the current at the various times. The derivative highlights the changes during the active phase in the surface photochemistry, and may aid in contaminant species identification. The origin begins at the instant that the shutter is fully open, and the time axis covers 4 sec after opening. Within that time frame, an initial photocurrent of approximately 0.4 arbitrary units occurs. This value holds to within a few percent for less than 0.5 sec. At that time, the collected current begins a rise, and lasts for about one second, after which it plateaus until approximately 2.4 sec, after which another transition to a higher collected current occurs. After about 3.5 seconds, the collected current begins to decline slowly. All examined specimens stored under normal conditions showed a similar sequence, although differences occur when different levels and types of contamination are present. For this particular contaminant reflected in FIG. 3, three peaks in the derivative were observed: one at a mean time of ~0.9 sec, one at ~2.7 sec, and one at ~3.6 sec. In other plots, activities at other time intervals were noted.

Figure 4A:
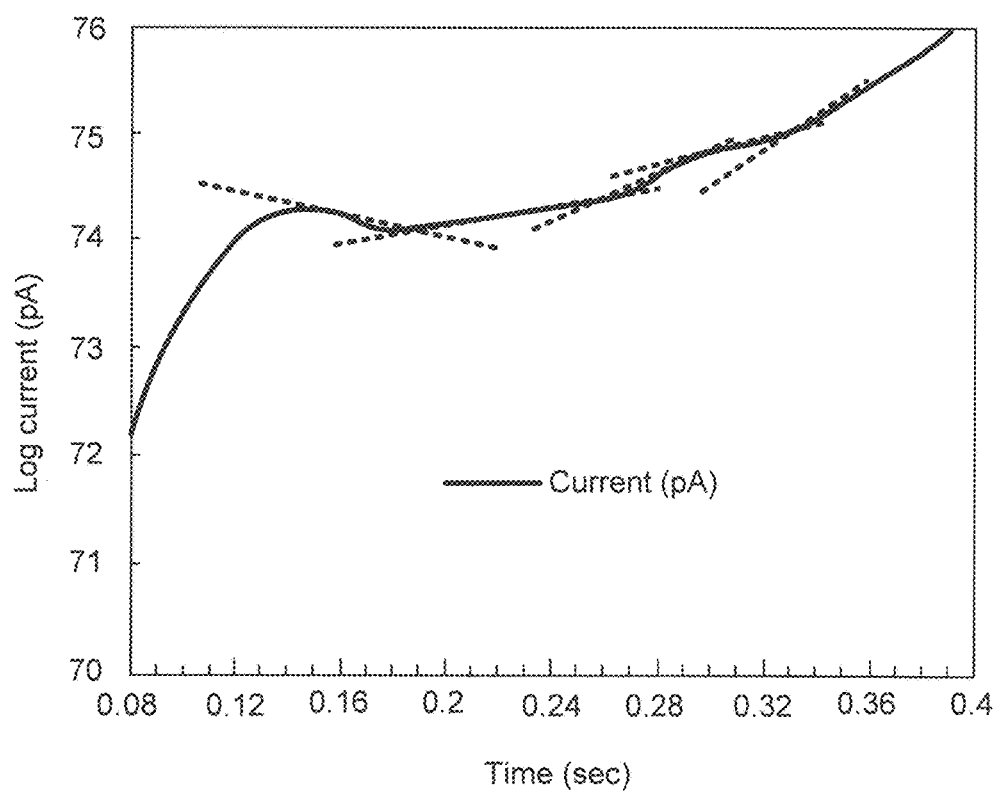
FIGS. 4A and 4B are graphs illustrating photo-induced active regions of collected currents.
Figure 4B:
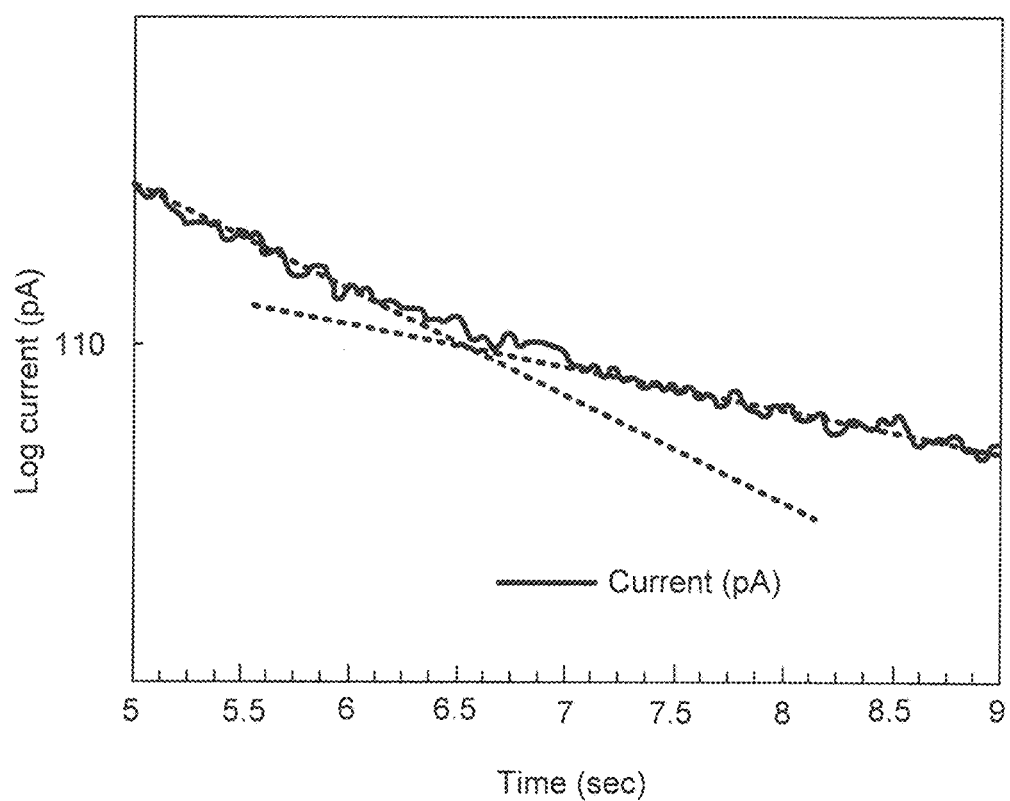

It is instructive to execute plots of log current vs time to aid in determining rate dependent based reactions. FIGS. 4A and 4B illustrate that a change in slope for two different segments of the current indicates a change in the reaction rates (related to decay constants) for the two active components in the contaminating substance on a cleaned substrate, indicating that a residual level of a specific contaminant remains on the cleaned surface. The first of these plots, shown in FIG. 4A, examines the beginning of the photo-induced active region of the collected current. Of particular interest is the sequence of line segments, each of a constant slope, that appear in succession. The slopes are related to the rates of the kinetics involved in the surface state chemistry induced by the ultra-violet intensity of the illumination. The slopes of the natural log (ln) of the current (ln(current)) change relatively quickly (~0.03 to several seconds) during the time intervals of monitoring.

As an experiment, two specimens were cleaned according to a standard cleaning method. Then the following was performed: 1) one of the two specimens (Specimen 2) was contaminated with a measured level of contaminant; 2) both specimens (the contaminated specimen, and the clean "reference" specimen (Specimen 1) were placed in an embodiment OSEE measurement system and charge emission was measured on each as a function of time for approximately 10 seconds, 3) Specimen 1 was further subjected to a "vapor" cleaning technique, and then re-measured with the embodiment OSEE instrument. The above experiment provided three data sets from the original two specimens for analysis. First, the initial photoemission immediately after the shutter is fully open (approximately 80 msec after the shutter was activated) was recorded. The reading in pA for Specimen 2, the contaminated specimen was 25.1 pA, the reading for Specimen 1 (the reference) was 122 pA, and the reading for Specimen 1 when vapor degreased (the reference vapor degreased) was 156.5 pA. The cleaning technique makes a difference in the photo current reading. It may be assumed that the higher the photo current reading, the cleaner is the surface, although in reality this may more realistically represents a lower effective work function. Of more significance are readings from the uncontaminated specimen, Specimen 1. This surface condition after cleaning followed by vapor degreasing may be deemed as representing the "most clean state" of the surface.

Figure 5:
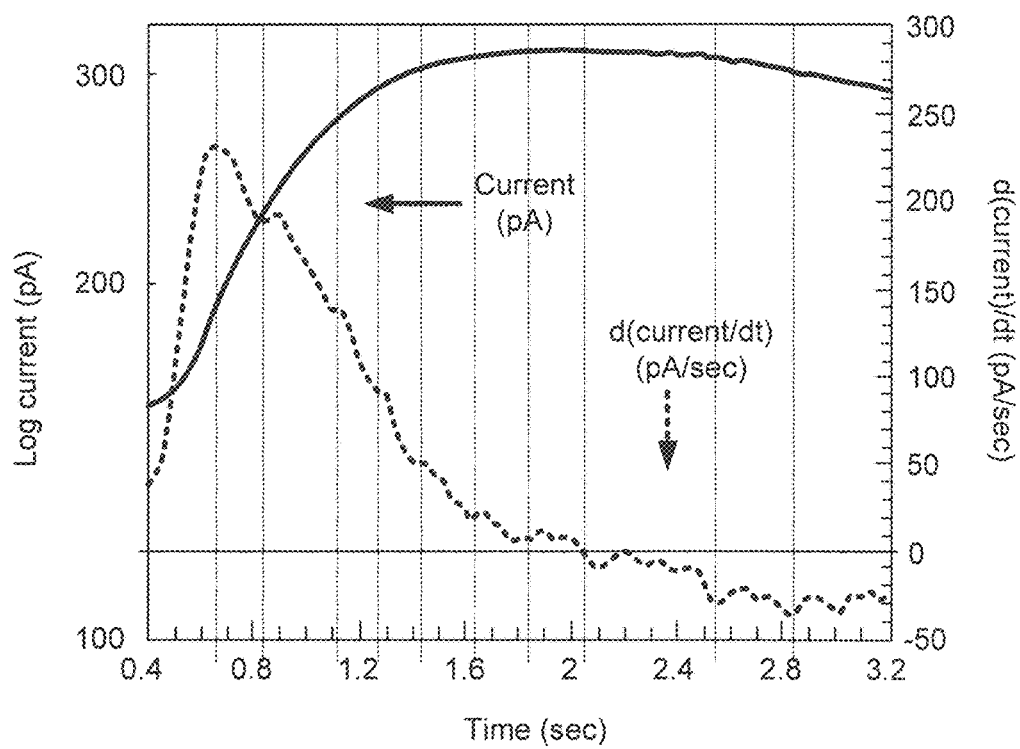
FIGS. 5, 6, and 7 are plots of measurements by an embodiment OSEE device or instrument of current in pico-Amps on a logarithmic scale and the time derivative of the current in picoamps per second versus time.

FIG. 5 is a plot of OSEE current and its time derivative. FIG. 5 is a plot of OSEE current in picoamps on log scale (left axis) and its time derivative, d(OSEE Current)/dt in picoamps/sec (right axis) vs. time for a vapor degreased specimen. Vertical lines mark central locations of slopes in the current. The log current is sensitive to the rates of chemical reactions of the various chemical species in the contaminant, and can aid in identifying the chemical species in the contaminant. The specimen was cleaned according to the usual wipe technique, and then vapor-degreased. The graph begins 0.4 seconds into the data collection cycle, and ends later at 3.2 seconds into the cycle. The time derivative is relatively simple, with small relative peaks appearing after the major peak, of approximately 250 pA/sec (~0.67 sec into the data collection). The actual current rises from ~130 pA (at 0.4 sec) to ~305 pA (at ~2 sec), and then falls to ~290 pA (at 3.2 sec).

Figure 6:
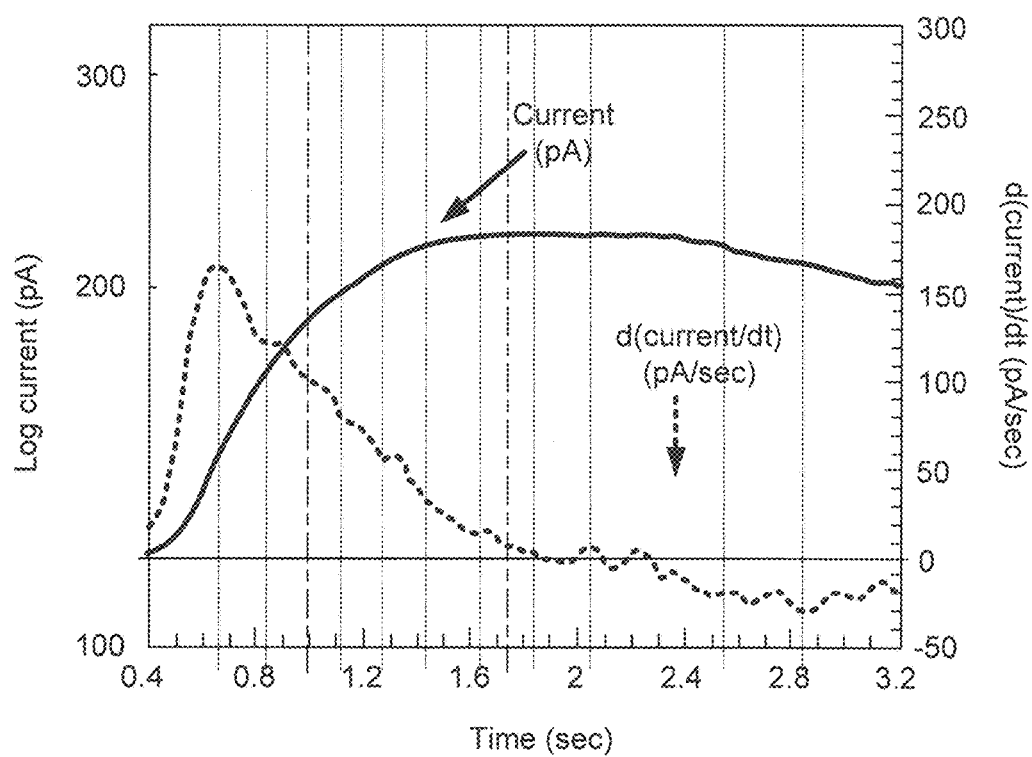

FIG. 5 can be contrasted with the current record from the specimen cleaned in an ordinary way (with a moistened wipe only) as shown in FIG. 6. FIG. 6 is a plot of collected current in pico-amps (left axis) and its time derivative, d(Current)/dt (right axis) vs. time for a specimen cleaned in an ordinary way. The time derivative of the current, while lower, has differing structure at various times, when compared to the specimen that is also vapor-degreased. The actual current rises from ~110 pA (at 0.4 sec)) to ~205 pA (at ~2 sec), and then falls to ~200 pA (at 3.2 sec).

Figure 7:
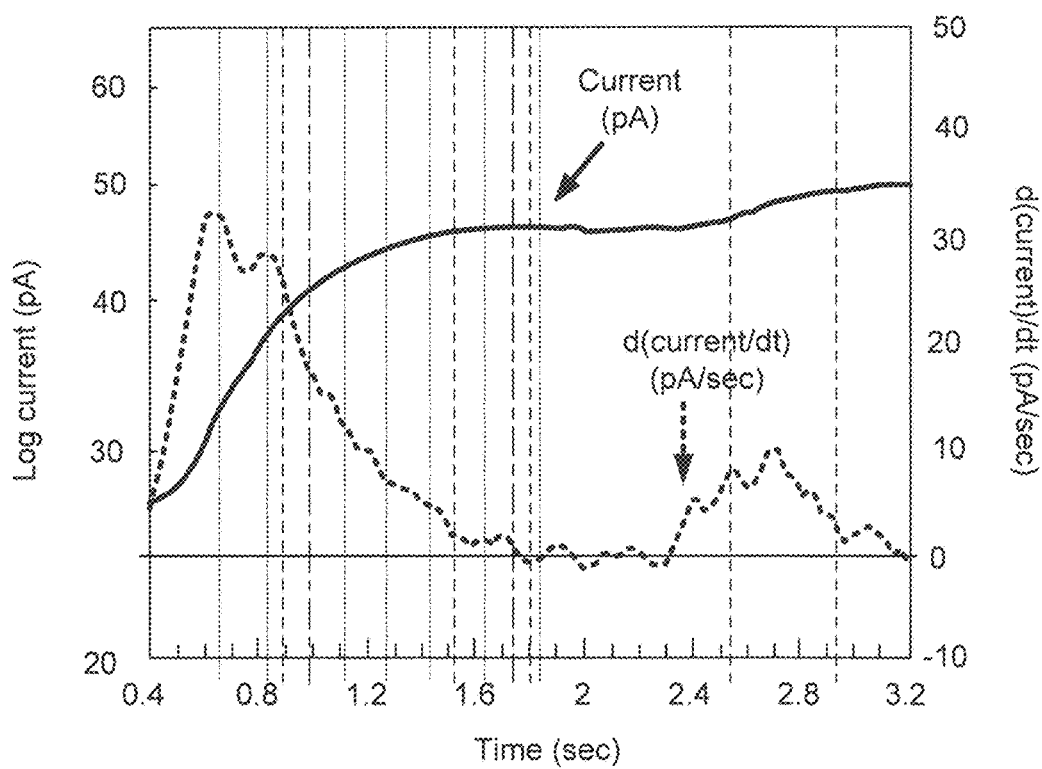

Finally, the plots of Specimen 2 (the contaminated specimen), are shown in FIG. 7. FIG. 7 is a plot of OSEE current in picoamps (left axis) and its time derivative, d(OSEE Current)/dt (right axis) vs. time for a contaminated specimen. The vertical lines are locations of changes in the time derivative of the current. For emphasis, the 0 line of the derivative is also highlighted with a horizontal line. The time derivative of the current, is substantially lower than either of the cleaned specimens. Additionally, the time derivative shows/has differing structure at various times, when compared to the specimens including the one that is vapor-degreased. The actual current rises from ~22 pA (at 0.4 sec) to ~43 pA (at ~2 sec), and then rises to ~48 pA (at 3.2 sec). A substantial difference between the derivatives of the waveforms, when clean versus those waveforms from a contaminated specimen was observed. These differences are further examined to aid in identification of concentration and species of contaminants.

Kinetics Analysis and Differential Form of Rate Laws.

Rate laws may be used to describe the rate change of a reactant concentration with time. For demonstration assume that the reaction rate directly affect the photostimulated current measured by collection of separated charges. For example, both the photo-dissociation of molecules into ionic components, and the emission of electrons from a substrate (photoelectric effect) are collected and measured as a current by the embodiments of the OSEE device. Hence, the measured current contains results from reactions caused by the ultraviolet radiation flux impinging on the surface and the contaminants that reside there. As discussed above, the log plots of the current in time provided regions where the line segments were essentially straight, as shown in FIGS. 4A and 4B. Since this is modeled as having the properties of adsorption and desorption, these line formations may indicate the order of the rate process outlining the related kinetics. In this case, the indication is that of a first order rate process in its most straightforward form. However, simple plotting routines can be used to identify the reaction order.

To illustrate this connection it may be helpful to use the fact that log plots of the current reveal a number of straight-line segments connected by short transitions as shown in FIGS. 4A and 4B. Such a characteristic is indicative of a first-order effect for the example shown.

Figure 8:
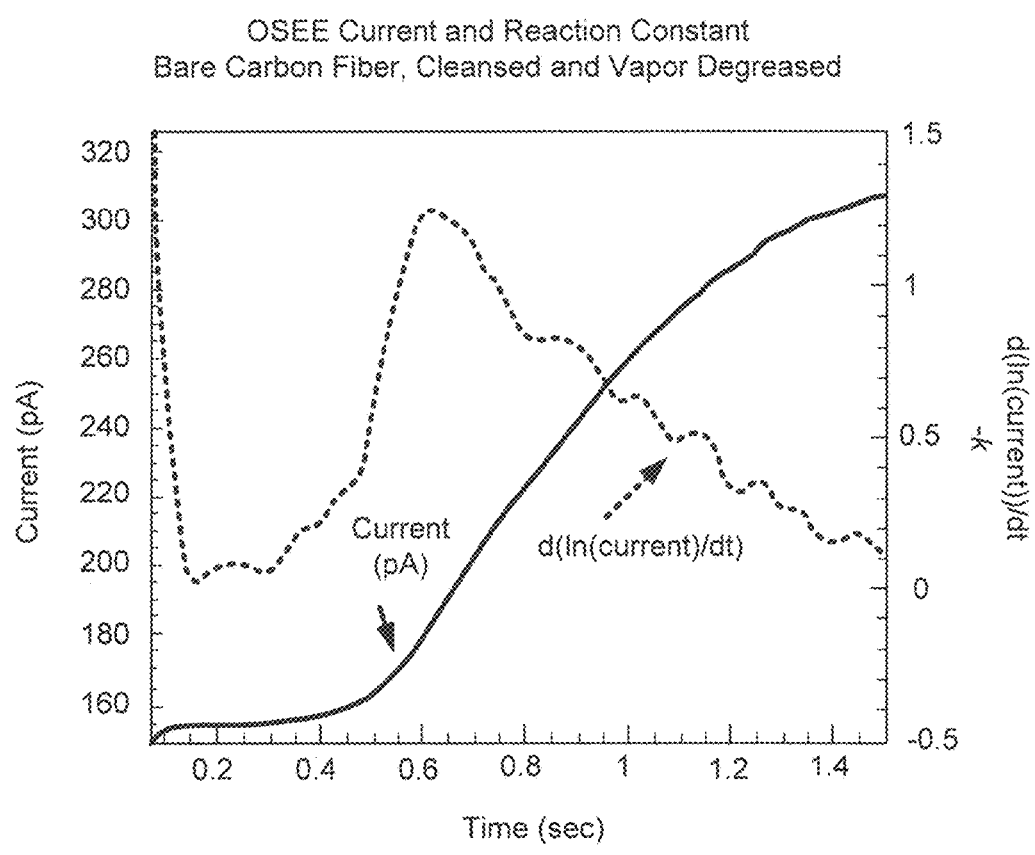
FIGS. 8, 9, and 10 show the reaction rate, k, for a substrate of bare carbon fibers with the surface cleaned two different ways and the surface purposely contaminated after cleaning, respectively.

For these illustrations presented here, the differential form of the relationship between the reaction rate, k, and the collection current may be considered. The components in the surface contaminants undergo an irreversible reaction path (IRP), which is activated to a series of excited states by the frequencies in the excitation illumination (e.g., the mercury spectrum). These excited states change local work functions even more, and thus make possible an incremental change in the collected photocurrent. Hence, this incremental change is linearly related to the concentration of excited states of the contaminant. Therefore the current variation tracks the excited contaminated concentrations, and the contaminant species may be determined by examination of the time dependence of the effective reaction rate constant, k, according to the equation $$k(t) = -\frac{1}{[B]} \frac{d\ln[A^*]}{dt} = -\frac{\mathcal{G}}{[B]} \frac{d(\ln j)}{dt} \quad (1)$$

where j is the photocurrent density (current/area), [B] is the exciting photon numerical current density (note: this is the concentration of the photons of a given frequency that cause the photoemission), [A*] represents the concentration of excited states, which may be caused by a photon-atom interaction that is not necessarily associated with the photon density responsible for photoemission, and $\mathcal{G}$ is a proportionality constant. This means that the derivative, $$\frac{d\ln j}{dt}$$

tracks me reaction rate between [A] and [A*]. A plot of the derivative (an example of which is shown in FIG. 8 discussed below), behaves in time just as the negative of the rate constant within a constant of proportionality (assuming that [B] and $\mathcal{G}$ are constants). The rate is calculated by taking the natural logarithm of the current data, followed by the numerical derivative. A plot then shows the reaction rate as a function of time, and changes are noted as indications of changes in the reaction. The data reveals a series of complex chemical reactions that depend on the luminous wavelength composition and the associated flux.

Analysis shows that the reactions vary over time. The early reactions start with the reaction rate k is close to zero, but with some structure. Then in about 500 msec, the rate quickly rises to greater than 1, followed by a decrease toward zero. Again, some structure in k becomes visible as it decreases toward zero and the current rises toward a maximum value. Depending on the contaminant species and its concentration level, other changes in the reaction rate occurs, since the plot of k is a composite of all reaction rates occurring in time.

Figure 9:
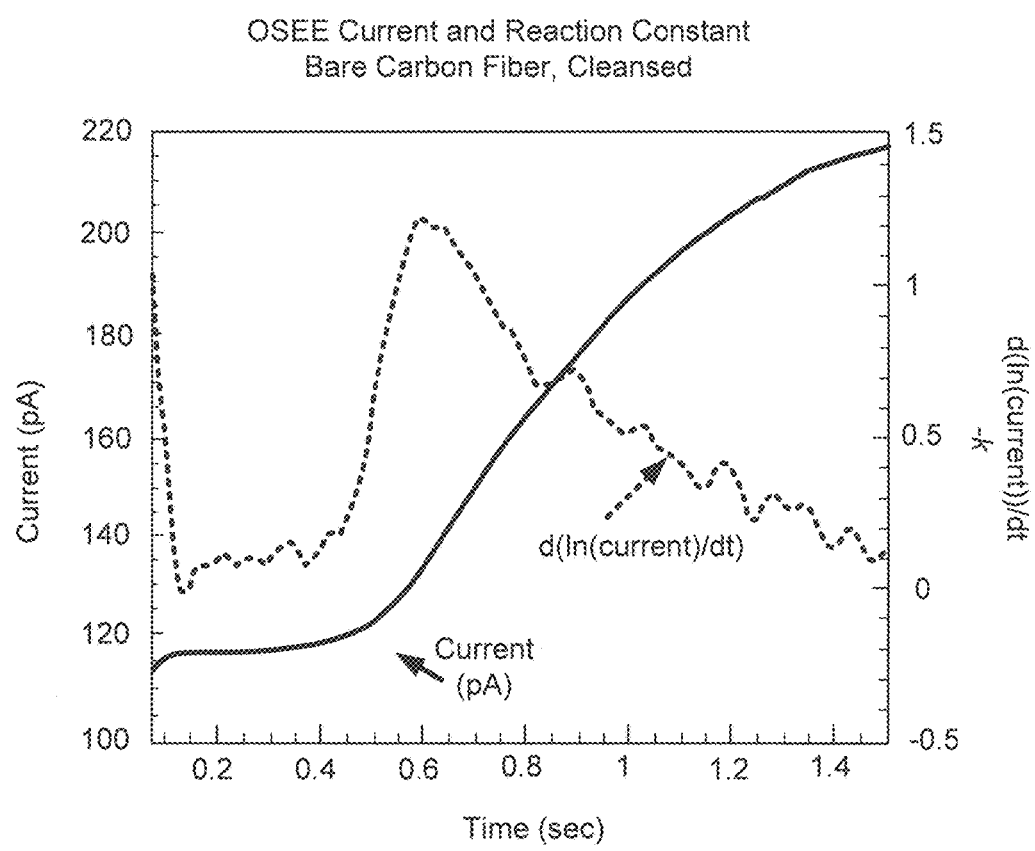

FIG. 8 shows k for a substrate of bare carbon fibers as might occur in composite structures, with the surface cleaned two different ways. The surface represented in FIG. 8 was cleaned by vapor-degreasing, and the surface represented in FIG. 9 was cleaned by wiping with a cloth or paper wipe saturated in a solvent. FIG. 8 illustrates the collector current (OSEE and charge dissociation) and reaction rate as a function of time. The reaction rate is calculated from the time derivative of the log plot of the collector current as a function of time. This plot is over the time interval from 0.08 seconds to 1.5 sec. and the substrate is bare carbon. FIG. 9 plots the reaction rate as a function of time of bare carbon fiber surface composite structure. This differs from the plot in FIG. 8 in that the surface was wiped clean, only using the same protocol adopted for the vapor-degreased specimen of FIG. 8 without vapor-degreasing. This is calculated from the time derivative of the log plot of the OSEE current as a function of time. This plot is over the time interval from 0.08 seconds to 1.5 sec. Of note is that the k has a slightly different structure in both cases, with more structure appearing on the substrate wiped with a solvent-impregnated wipe. This would indicate that the vapor-degreased surface is cleaner.

Figure 10:
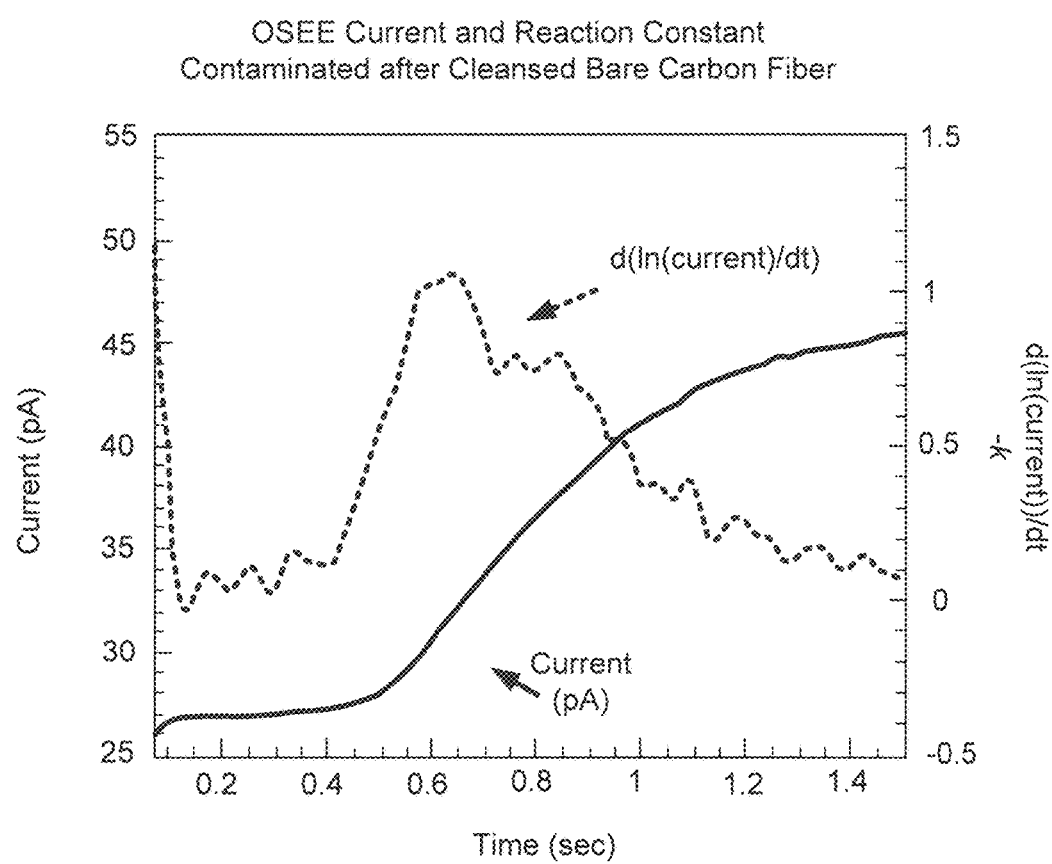

FIG. 10 shows a plot of k from a surface purposely contaminated after cleaning. FIG. 10 plots the reaction rate as a function of time of bare carbon fiber surface composite structure, contaminated on the surface. The surface was initially wiped clean, using the same protocol adopted for the specimen shown in FIG. 8. This is calculated from the time derivative of the log plot of the OSEE current as a function of time. This plot is over the time interval from 0.08 seconds to 1.5 sec. In this case, an obvious and substantial increase in the structure of k occurs. This structure gives information about how the contaminants might react on the substrate surface in the presence of ultraviolet flux as a function of time. Further, as the contaminant increases, the collection current decreases as expected.

When compared to the specimen cleaned by the wipe technique, the reaction constant of the vapor-degreased specimen has less structure. Some additional structure, as indicated by a change in depth and increase in inflections, relative maxima and minima, and higher frequency components show up in the wiped surface method of cleaning. This is noted not only around the peak and after, but also in the time interval in the first several hundred milliseconds after the shutter opens. The structure increase is associated with an increase in remaining contamination.

Figure 11:
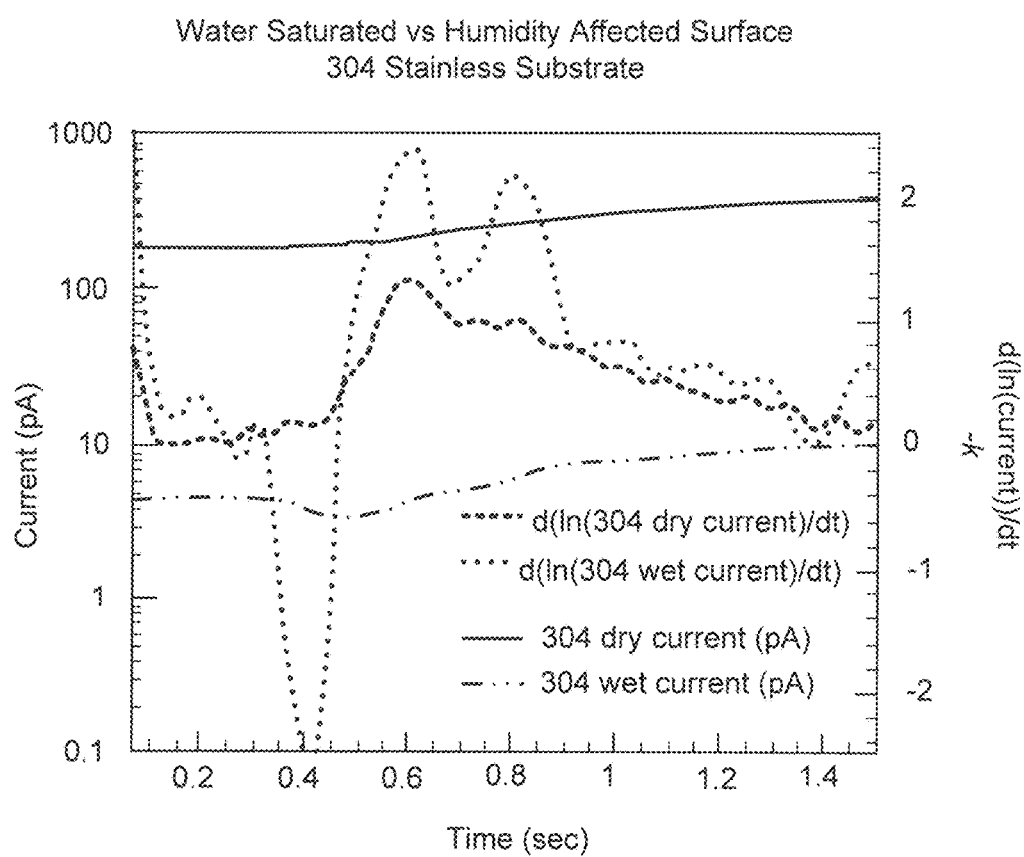
FIG. 11 is a graph of collector current and the reaction rate as a function of time.

Humidity is always present, since air has water vapor as a constituent. It is well known that water molecules are always in a dynamic equilibrium with a surface over the temperature ranges encountered terrestrially. A specimen from a stainless steel alloy was prepared, vapor degreased, and exposed to air. The specimen was placed in the embodiment instrument's chamber, and the current was measured as a function of time. Then the specimen was saturated with water, and re-measured with the instrument. The results are shown in FIG. 11. FIG. 11 is a graph of collector current, (including OSEE from the substrate and charge emission), and the reaction rate as a function of time. This is calculated from the time derivative of the log plot of the collector current as a function of time. This plot is over the time interval from 0.08 seconds to 1.5 sec and the substrate is 304 Stainless Steel. Approximately 2 order-of-magnitude difference is seen in the collected current. Yet the plot of k is nearly the same, despite the difference in water concentration on the surface. Thus, k is shown to be largely independent of concentration, as expected.

The various embodiment techniques may allow measurement based on optically stimulated electron emission from even modestly concluding surfaces, including metals, carbon-based composites (carbon fibers, high-density carbon nanotube impregnated polymers), epoxies, paints, etc. The various embodiment techniques described herein may differ from the instruments and methods outlined in U.S. Pat. Nos. 5,393,980 and 6,856,403, in that the various embodiments may enable the following: 1) utilizing current-time relationships to aid in identification of contaminant species attachments to the substrates; 2) using correction techniques to compensate for humidity-affected measurements taken on surfaces without purge gases (i.e. measurements made in air and where water molecules adhering to a surface cause no problems with bond integrity, or may even help with strong bond formation); 3) testing for complex surface-related chemistries where water molecules, sulfides, and even hydrocarbon contaminants are involved.

Dipole Activation

In various embodiments, the property that electric fields orient electric dipoles may be used to provide identification of contaminant species. The electric field and dipole orientation couple together to change the molecular attachment energy state. This change in energy shifts the transition probabilities so that the substrate's regional work function is affected. Changing the electric field with an AC signal makes it possible to monitor this coupling. Because dipoles are integral parts of many molecules, dipoles may enable identification of the species and the concentration/coverage. Because the effect may be small, synchronous detection (i.e., lock-in amplification techniques) may be combined with dipole activation to measure the effect of the coupling of the electric fields and electric dipoles. The use of lock-in amplifier techniques extend sensitivities to dipole-induced coupling of adsorbent with substrate. In this manner, these techniques may be responsive to adsorbent attachments through physisorption processes and chemisorption processes.

In an embodiment, to measure dipole activation an AC voltage of amplitude $V_0$ may be applied to grid bias (e.g., by applying an AC voltage of amplitude $V_0$ to grid 114 described above with reference to FIG. 1A) in series with the collector voltage through the grid bias (e.g., through gird bias power control 160 described above with reference to FIG. 1B) or in series with the grid bias power (e.g., the Grid Bias Power input to the Voltage Converter 108 as described above with reference to FIG. 1A). The collector current, i, may be converted into a voltage signal by a voltage converter (e.g., Voltage Converter 108 as described above with reference to FIG. 1A). The collector current, i, may be affected by the AC voltage and may be analyzed separately from the DC current.

Starting with the current versus voltage from Langmuir-Child analysis with negligible electron cloud density near the photo-cathode, the following may be determined:

$$i \sim V^{\frac{1}{2}} \quad (2)$$

Applying a voltage in series with the grid power supply may result in the follow:

$$V = V_0 \left( \frac{1 - \cos 2\omega t}{2} \right) \quad (3)$$

where ω is a programmed reference frequency and t is time. By using a trigonometry equivalence statement, the effect of the voltage addition to the photocurrent consistent with Eq. (2) is $$V^{\frac{1}{2}} = V_0^{\frac{1}{2}} \sqrt{\frac{1 - \cos 2\omega t}{2}} = V_0^{\frac{1}{2}} \sin \omega t \quad (4)$$

Hence, the effects of dipole action may be separated within a contaminant under the action of a varying field. Depending on the polarizability, α, the current associated with a variation of the dipole concentration is isolated by using synchronous detection (e.g. a lock-in amplifier arrangement) as follows:

$$i_{AC} = i_\alpha \sim \alpha V_0^{\frac{1}{2}} \quad (5)$$

Therefore, the current will have contributions from both the DC potential provided by the grid bias supply, as shown in FIG. 1A, and from the applied AC voltage applied in series with the grid bias supply.

For measurement an AC applied voltage of frequency, 2ω, is added in series to the bias supply. At the same time, a programmed reference frequency, ω, and the detected photocurrent, i, are sent to the lock-in amplifier to measure the current fluctuation, $I_0 \sin(\omega t - \phi)$. This measurement aids in the identification of the contaminant species, including those species with an atomic polarizability, α.

As an example, consider a contaminant of density ρ and thickness z on a substrate. The contaminant's areal density, σ, is:

$$\sigma = \rho z \quad (6)$$

From the Debye Equation that includes the Langevin term for polar molecules of strength, p, the magnitude of the areal density of the dipoles, $P_\sigma$, (a vector) becomes:

$$P_\sigma = n z \left( \alpha + \frac{p^2}{3kT} \right) \left( \frac{k_e + 2}{3} \right) \frac{V}{d} \quad (7)$$

where n is the numerical density (# of molecules/Volume) of the polar molecules, V is the applied voltage to the plate and is the sum of the DC and AC amplitude contribution, ($V^{1/2}$ from Eq. (4)), d is the separation between the substrate (e.g., substrate 112 in FIG. 1A) and the collector plate (e.g., grid 114 in FIG. 1A). $k_e$ is the dielectric coefficient of the contaminant.

In the presence of the applied electric field, each orientation may be separated into an energy differential, ΔE, by:

$$\Delta E = -\int_{Surface} P \cdot E dS \quad (8)$$

where the magnitude of the electric field vector, E in Eq. (8)=V/d in Eq. (7). This separation allows for the transitions among states, which absorbs energy, and causes a change in signal strength in step with the frequency ω.

Note that Eq. (7) indicates a temperature dependence in the orientation of the polar term. Therefore, by changing the temperature of the specimen, the contributions from polar molecules and those polar effects arising from the presence of the electric field may be separated (when expanded, the term containing α).

Thus, the current amplitude at frequency ω, $I_0(\omega)$, shows the effects of the dipole coupling on the substrate's work function, and depends upon substrate and the contaminant species. Moreover, the effect of the dipole concentration on the signal depends upon the thickness, which is measured by the Beer-Lambert law, and properties of the specific contaminant. Therefore this measurement contributes to the identification of the contaminant species, since α, $k_e$ and p may be "markers" for a suspected contaminant.

Separation of Multiple Contaminant Effects on OSEE Readings

In the presence of multiple wavelengths of electromagnetic radiation, as occurs with, for example, the mercury spectrum, attached contaminant molecules undergo reactions (including those associated with configuration changes) and thus change their attachment patterns with the substrate. Each reaction has its respective reaction rate. These reactions are occurring in the measurement's time frame (that time interval from when the illumination process starts to when the photocurrent reaches a steady state). The daughter products of the early reactions become the principles in later reactions. Hence, there is a composite reaction rate that changes in time. Because of the nearly linear relationship of the substrate's work function to changes in contaminant surface concentrations, the photocurrent tracks changes in the composite reaction rate at which the transformation products are formed.

In an embodiment, a curve fitting technique may be used to separate effects of multiple contaminants by measuring the reaction constant as shown through the contaminant coupling with the change in the substrate work function.

As discussed above, the current variation tracks the excited contaminated concentration, and the contaminant species may be determined by examination of the time dependence of the effective reaction rate constant, k, according to Eq. (1).

The plot of −k (see e.g., FIG. 8 discussed above) shows the superposition of an assortment of various contaminant species, each with different contributions to the plot. For the sake of illustration, assume that the interaction begins at $t = t_0$. A simplified form for k(t) for a contaminant of reaction amplitude, $\mathcal{C}$, may be as follows:

$$k(t) = H(t - t_0) \mathcal{C} e^{-(t - t_0)} \quad (9)$$

where H is the Heaviside Step Function, $\mathcal{C}$ depends upon contaminant coverage of substrate, θ, [B] is the numerical current density of the exciting photons. Implicit in these variables are matrix terms involving the atomic interactions between the substrate and the contaminant species, coverage etc. all of which affect results.

Figure 12:
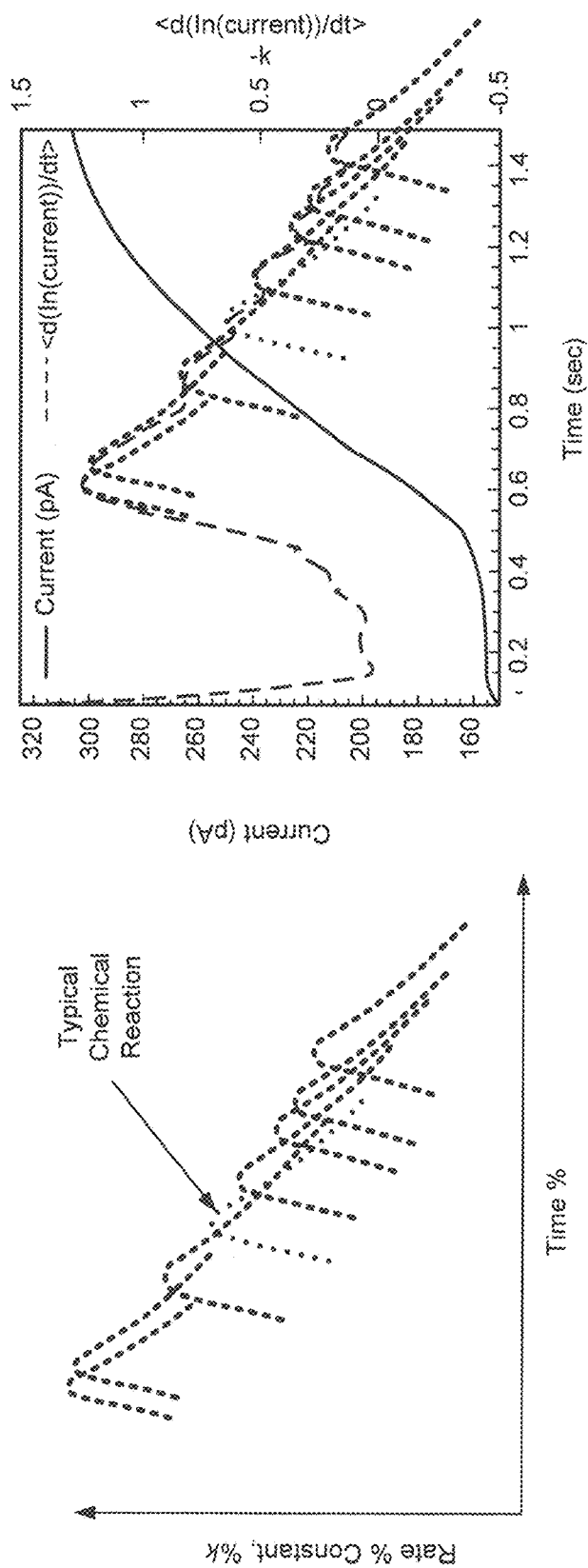
FIG. 12 is a composite plot of reactions taking place on a typical substrate under exposure to electromagnetic radiation.

Consider a composite plot of Eq. (9) as shown in FIG. 12. FIG. 12 is a composite plot of reactions taking place on a typical substrate under exposure to electromagnetic radiation, which contains multiple frequencies, with at least one frequency contributes to photoelectron emission from the substrate. Note that the composite is the sum of reactions occurring on the surface.

As in the case above, the presence of multiple wavelengths of electromagnetic radiation, as occurs with, for example, the mercury spectrum, attached contaminant molecules undergo physical and chemical changes (reactions), and thus change their attachment patterns with the substrate that varies in time. Each reaction has its reaction rate with a consequent frequency distribution in the Fourier transformed space. The composite reactions, which change in time, also exhibit a pattern that changes with frequency. Since the substrate's work function changes with contaminant surface concentration, the Fourier transform of the photocurrent tracks changes in the frequencies of the composite reaction at which the transformation products are formed. This also contains factors that are related to species type and species concentrations. The Fourier transform of the –k vs t curve separates out the variations in the –K vs. ω curve, and permits the analysis of the concentration and its identity through frequency analysis provided by the transform.

In an embodiment, curve fitting may be used to separate effects of multiple contaminants by measuring the reaction constant as shown through the contaminant coupling with the change in the substrate work function. For example, the Fourier Transform of k(t) in Eq. (9), K(ω), is:

$$K(\omega) = Ce^{i\omega t_o}\left[\frac{1-i\omega}{1+\omega^2}\right] \quad (10)$$

Figure 13A:
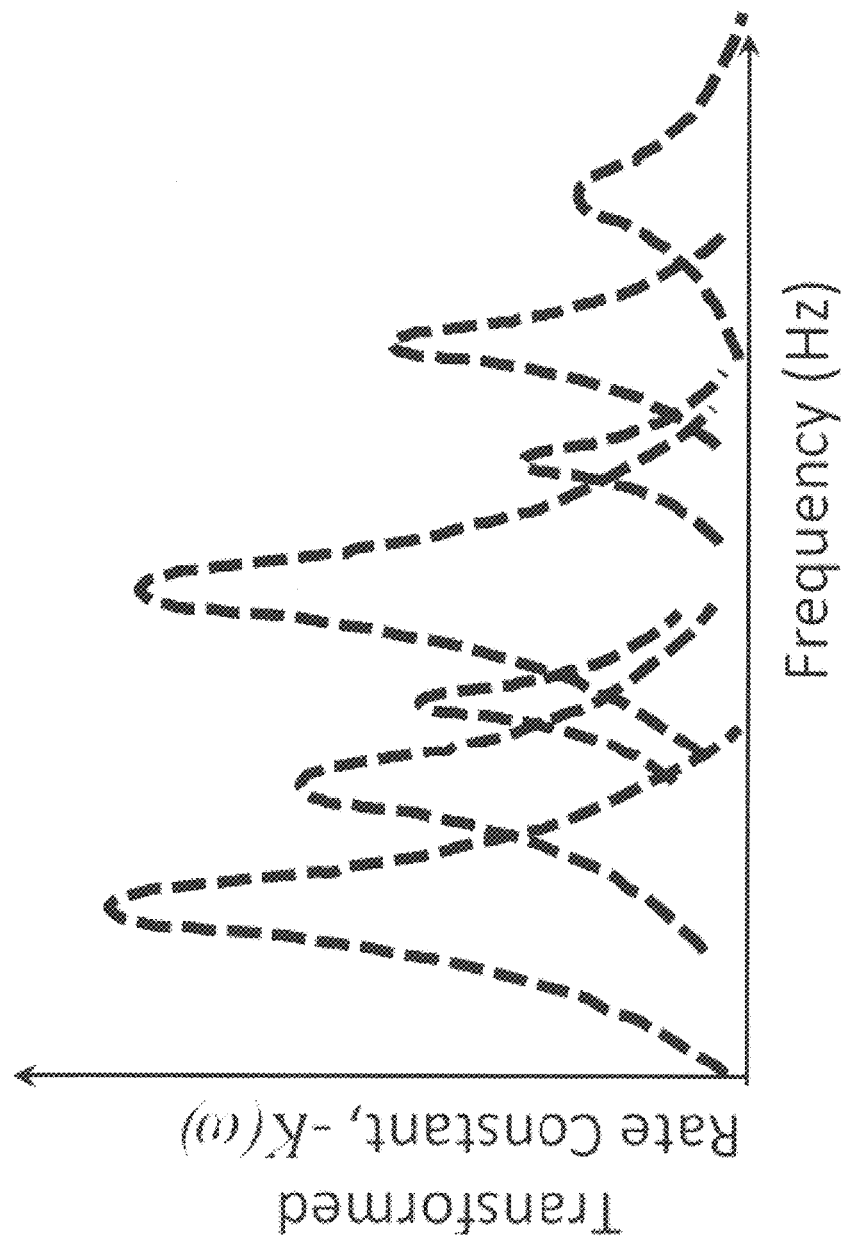
FIG. 13A is a schematic of a plot of the Fourier transform of the rate constant.
Figure 13B:
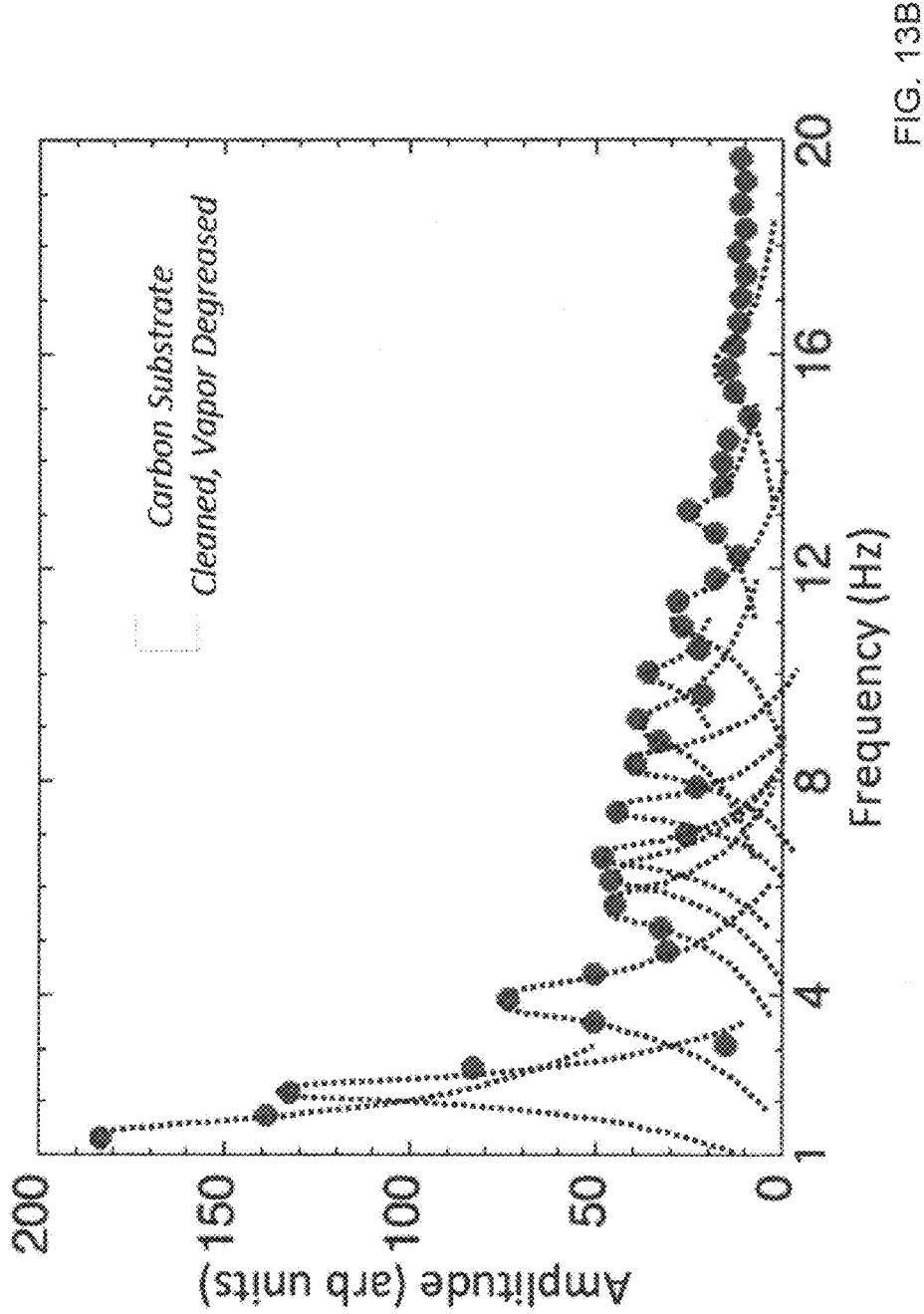
FIG. 13B is a schematic plot of the fit of the transform of individual reactions.

A plot of the Fourier Transform of the reaction function, Eq. (9), is schematically shown in FIG. 13A. FIG. 13A is a schematic of a plot of the Fourier transform of the rate constant. The amplitude of each component is proportional to the concentration. The Fourier transform from data taken on a "cleaned" specimen (with some residual contamination remaining) is shown in FIG. 13B. FIG. 13B is a fit of the transform of individual reactions to data taken on a "cleaned" carbon substrate. The specific contaminant concentration and its contribution to the rate constant (the larger the contribution, the smaller the reaction time interval) directly affects the character of the –K vs. f curve. The amplitude depends on the concentration of the contaminant during the frequency interval. Hence, the frequency depends upon the transformed rate constant, K, and the concentration, $\mathcal{C}$, as shown in Eq. (10). Therefore, the separation between the different contributions directly depends upon the phase constant $e^{i\omega t_o}$, which is related to the "start time" $t_0$ of the Heaviside function. The height depends upon $\mathcal{C}$, and the band-pass of the electrometer circuit (e.g., voltage converter 108 discussed above).

Gas-Carrier Techniques to Identify Contaminant by Surface Reaction

Figure 14:
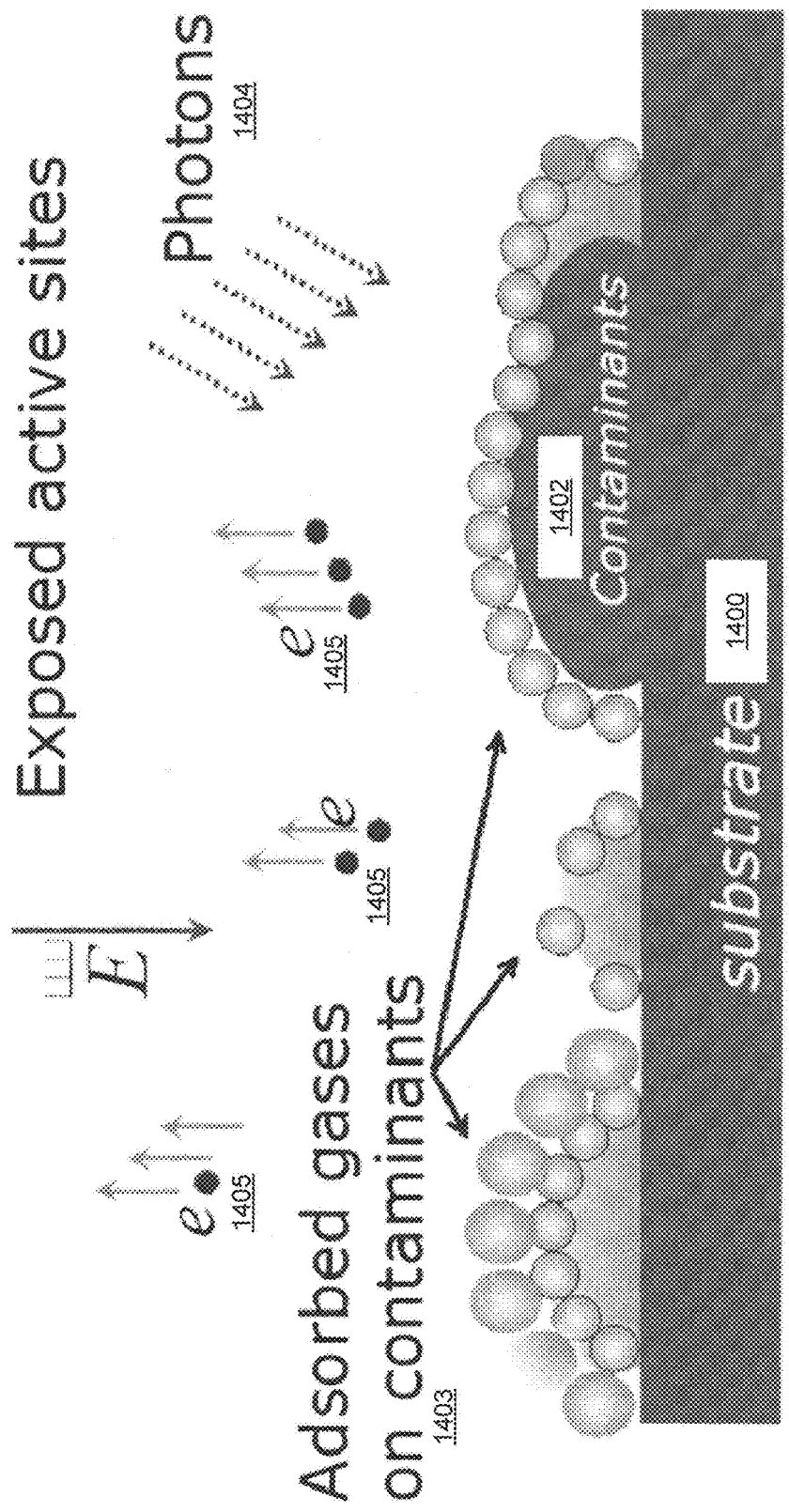
FIG. 14 is a schematic of a substrate containing various contaminants.

A particular contaminant may be sensitive to a particular reactant that can be introduced in a gaseous form. In an embodiment, by introducing the known reactant, the schematic of which is shown in FIG. 14, and monitoring the reaction by monitoring the photocurrent and using the analysis above, the particular contaminant may be identified. In another embodiment, any changes in gases given off during the photo-activation process may be monitored, such as by using gas chromatography, mass spectrometry, or other techniques to identify the particular contaminant. FIG. 14 shows a substrate 1400 containing various contaminants 1402. Gases 1403 that are reactive with the contaminants 1402 are introduced to attach to a specific contaminant 1402. Specific gas concentrations of species may be chosen for adsorption on specific contaminants. Adsorbed gas may indicate the presence of a contaminant species. Photons 1404 of various frequencies are chosen to release the attachment from a suspected contaminant 1402, thus verifying the contaminant 1402 presence. In another embodiment, additional photons are added to also release photoelectrons 1405, where the photocurrent responds to the work function change caused by the contaminant concentration changes brought about by the contaminant-gas reaction. Exposure of the contaminant to multi frequency electromagnetic radiation (EMR), where (1) at least one frequency provides photoemission from the substrate, and (2) the EMR frequencies provide energies for excitations of the consequent surface reactions. The time dependence of electron emission current determines contaminant content and concentration. As with the previously discussed techniques, the electric field, E, collects the electron emission, shown as e in FIG. 14.

Photo-Spectral Calibration of Response to Contaminant Thickness

A standard reproducible surface such as the face of a single crystal (e.g., a Silicon (100) surface) may be used as a reference surface (RS) to calibrate the response to contaminant thickness. The RS may be cleaned by using sequential techniques normally including a vapor-condensation on the reference surface as one of the final steps. A contaminant may be dissolved in a solvent to make a solution of a known concentration. A known volume of this solution may be uniformly applied onto the RS, and the solvent may be evaporated from the RS, leaving behind a known thickness of contaminant. Using the instrument as shown in FIG. 1A or 1B, or a variation of substantially similar function (such as an instrument with a single frequency emitting light source), the photocurrent may be measured in an inert atmosphere (e.g. dry argon) or a vacuum on an assorted set of cleaned specimens that have been contaminated, each with a different and known thickness of contaminant. This may allow for the measurement of the change in work function brought about by the contaminant by comparing the extrapolated current at contaminant deposition thickness=0 to the measured photocurrent of a clean substrate.

Using the Beer-Lambert Law:

$$I = I_0 e^{-\mu x}$$

$$i = i_0 e^{-\mu x} \quad (11)$$

where I is the illumination intensity, i is the corresponding photocurrent from the illumination intensity, x is the thickness of the (deposited) contaminant, and μ is the absorption coefficient, $i_0$ may be measured two different ways. The first value may be directly measured using a cleaned blank of RS. The current $i_0$ may be directly proportional to the photoemission caused by photon light intensity $I_0$. The second way may be to measure the photocurrents through the different contaminant thicknesses, and calculate a least-squares fit to the data plot of photocurrent (y-axis) against contaminant thickness (x-axis). Extrapolation to zero contaminant thickness gives a value for $i_0$, but for the condition of surface contamination approaching 0. A difference between the value of $i_0$ from these two different techniques may be expected, since the extrapolated value includes a change in the work function caused by the contaminant presence.

In an embodiment, the technique may be used to control the thickness of a reactant applied to a surface. In that case, the reactant may be designed or chosen to react with an adherent to form strong chemical bonds with the surface and near-surface atoms or to encourage chemisorption by atoms in the substrate with atoms in the adherent. This technique and refinements lead to the optimum concentration for best bond strength by providing the correct concentration of reactant on the surface. As above, using the Beer-Lambert Law and the above discussed arrangement, the optimum amount deposited on the surface to maximize strong-bond surface density may be measured.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

In the various embodiments described herein the functions described may be implemented in hardware, software, firmware, or any combination thereof. If implemented in software, the functions may be stored as one or more instructions or code on a non-transitory computer-readable medium or non-transitory processor-readable medium. The steps of a method or algorithm disclosed herein may be embodied in a processor-executable software module which may reside on a non-transitory computer-readable or processor-readable storage medium. Non-transitory computer-readable or processor-readable storage media may be any storage media that may be accessed by a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a processor. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. An optically stimulated electron emission (OSEE) measurement device, comprising:
    a power supply;
    a gas supply;
    at least one OSEE pod connected to the power supply and the gas supply, wherein the OSEE pod comprises:
        a light source connected to the power supply;
        a shutter;
        a grid connected to the power supply; and
        a gas nozzle connected to the gas supply; and
    a processor connected to the power supply, gas supply, and at least one OSEE pod, wherein the processor is configured with processor-executable instructions to perform operations comprising:
        controlling the gas supply to provide an inert gas to the gas nozzle to purge a chamber of the OSEE pod;
        controlling a first amount of power from the power supply to the light source to cause the light source to generate light;
        controlling a second amount of power from the power supply to the grid to bias the grid;
        opening the shutter such that the generated light floods a selected area of a sample;
        receiving a current measurement from the OSEE pod to determine a time dependence of a rate constant (k) using Equation (1) below:

$$k(t) = -\frac{1}{[B]} \frac{d\ln[A^*]}{dt} = -\frac{\mathcal{G}}{[B]} \frac{d(\ln j)}{dt}; \quad (1)$$

and
    analyzing the received current measurement to determine a level and a species of surface contaminants on the selected area of the sample by calculating from the received current measurement using Equation (1) a reaction rate of at least one of the surface contaminants with the light,
    wherein j is photocurrent density (current/area), [B] is exciting photon numerical current density, [A*] is concentration of excited states, $\mathcal{G}$ is a proportionality constant, and dlnj/dt is reaction rate between [A] and [A*].

2. The OSEE measurement device of claim 1, wherein the at least one OSEE pod further comprises an ultraviolet (UV) intensity monitor, and wherein controlling the first amount of power from the power supply to the light source to cause the light source to generate light comprises controlling the first amount of power based at least in part on a signal from the UV intensity monitor to maintain an intensity of the light at a selected level.

3. The OSEE measurement device of claim 2, wherein analyzing the received current measurement to determine the level and the species of surface contaminants on the selected area of the sample comprises comparing the received current measurement to a reference substrate data stored in a memory of the OSEE measurement device.

4. The OSEE measurement device of claim 2, wherein the at least one OSEE pod comprises at least two OSEE pods.

5. The OSEE measurement device of claim 4, wherein analyzing the received current measurement to determine the level and the species of surface contaminants on the selected area of the sample comprises comparing the received current measurement from a first OSEE pod to the received current measurement from a second OSEE pod.

6. The OSEE measurement device of claim 5, wherein the second OSEE pod is associated with a reference substrate.

7. The OSEE measurement device of claim 4, wherein the light source is one or more of an arc lamp, a tungsten lamp, a laser emitter, a light emitting diode (LED) emitter, a discharge tube, a flash tube, a mercury discharge source, and a light pipe.

8. The OSEE measurement device of claim 4, wherein an emission frequency of the light source is adjustable.

9. The OSEE measurement device of claim 4, wherein the inert gas is argon.

10. The OSEE measurement device of claim 4, wherein the OSEE pods are non-planer pods.

11. The OSEE measurement device of claim 10, wherein the OSEE pods are coaxial in structure with the light source axially aligned with a collector electrode.

12. The OSEE measurement device of claim 10, wherein the OSEE pods are circular.

* * * * *